United States Patent [19]

Hino et al.

[11] Patent Number: 5,372,574
[45] Date of Patent: Dec. 13, 1994

[54] ARTIFICIAL LIMB JOINT AND JOINT DEVICE

[76] Inventors: Takumi Hino, 137-18 Higashi-ishidate-cho; Yoshihiro Morinaka, 16-1 Atagomachi 2-chome, both of Kochi-shi, Kochi 780; Shosuke Shimokawa, 1773-1 Kamo, Sakawa-cho, Takaoka-gun, Kochi 789-12; Motoo Nojima, 272-8 Yokogawara, Shigenobu-cho, Onsen-gun, Ehime 791-02, all of Japan

[21] Appl. No.: 87,673
[22] PCT Filed: Nov. 12, 1992
[86] PCT No.: PCT/JP92/01478
§ 371 Date: Jul. 12, 1993
§ 102(e) Date: Jul. 12, 1993
[87] PCT Pub. No.: WO93/09734
PCT Pub. Date: May 27, 1993

[30] Foreign Application Priority Data
Nov. 14, 1991 [JP] Japan .................. 3-327110

[51] Int. Cl.⁵ .............................................. A61F 5/00
[52] U.S. Cl. .................................... 602/16; 602/26; 602/27; 16/342
[58] Field of Search ............... 602/16, 20, 23, 26, 602/27; 16/324, 333, 334, 342; 403/107, 106, 104, 103, 97, 98; 623/39

[56] References Cited
U.S. PATENT DOCUMENTS

| | | | |
|---|---|---|---|
| 3,517,965 | 6/1970 | Cowles et al. | 16/324 X |
| 4,320,747 | 3/1982 | Daniell, Jr. | |
| 4,433,679 | 2/1984 | Mauldin et al. | 602/16 |
| 4,620,532 | 11/1986 | Houswerth | 602/16 |
| 4,657,000 | 4/1987 | Hepburn | 602/16 |
| 4,738,252 | 4/1988 | Friddle et al. | 602/16 |
| 4,773,503 | 9/1988 | Purkapile | 403/97 X |
| 4,982,732 | 1/1991 | Morris | 602/16 |
| 5,074,290 | 12/1991 | Harris et al. | 602/26 X |
| 5,105,805 | 4/1992 | Lapointe et al. | 602/16 |
| 5,176,623 | 1/1993 | Stetman et al. | 602/16 X |

FOREIGN PATENT DOCUMENTS

| | | |
|---|---|---|
| 52-126983 | 10/1977 | Japan . |
| 58-11219 | 3/1983 | Japan . |
| 60-500847 | 6/1985 | Japan . |
| 62-2531 | 1/1987 | Japan . |
| 1-133911 | 9/1989 | Japan . |

Primary Examiner—Richard J. Apley
Assistant Examiner—Linda C. Dvorak
Attorney, Agent, or Firm—Armstrong, Westerman, Hattori, McLeland & Naughton

[57] ABSTRACT

An artificial limb joint device for hinging adjoining body protecting members to turn on an axis perpendicular to the longitudinal axes of the body protecting members. The limb joint device comprises: a drive disc; a driven disc; a joint pin extending through the individual centers of the drive disc and the driven disc. The drive disc is detachably attached to one of the adjoining body protecting members and includes an outer flange, and an inner flange disposed radially inside of the outer flange and defining an annular groove in the end face of the drive disc together with the outer flange. The outer flange is formed with a through hole extending in a tangential direction of the annular groove. The driven disc is detachably attached to the other of the body protecting members and formed with such a raised segment at the end face confronting the drive disc as to engage in a sliding manner with the annular groove of the drive disc. Further comprised is a turning motion regulating pin inserted into the through hole to come into and out of the annular groove, for regulating the turning motions of the raised segment in the annular groove.

17 Claims, 21 Drawing Sheets

ARTIFICIAL LIMB JOINT AND JOINT DEVICE

BACKGROUND OF THE INVENTION

1. Field of the Invention

The present invention relates to an artificial limb joint and a joint device using the limb joint and, more particularly, to an artificial limb joint and an artificial limb joint device, in which adjoining body protecting members are connected and borne in a manner to turn on an axis perpendicular to their longitudinal directions such that they can have their relative turning angle adjusted and fixed.

2. Description of the Prior Art

An artificial limb joint device according to the prior art is constructed, as shown in FIG. 27, so as to protect and aid the physical functions of a leg 110 by fixing the thigh above the knee by two bands 101 and 102, by protecting the knee by a protecting member 103, by fixing the calf below the knee by a band 104, by connecting the bands 101, 102 and 104 and the protecting member 103 by metal columns 105 and 106, and by connecting the metal columns 105 and 106 by a joint 107.

Shown in FIG. 28 is an artificial limb joint device 111 similar to the type manufactured by the United States Manufacturing Company which is constructed by attaching a joint 118 to an upper protecting member 112, which is applied to a portion 119 of a human body, by screws 115a and 115b, and by hinging the joint on a joint pin 118a between the upper protecting member 112 and a lower protecting member 113 attached by screws 116a and 116b. Thus, the limb joint device 111 is given a function to adjust the allowable range of the relative turning angle between the upper protecting member 112 and the lower protecting member 113.

However, the artificial limb joint device, as designated at 100 in FIG. 27, is accompanied by problems that its weight is increased because it is combined with the metal columns and that the allowable range determined at the manufacture time cannot be changed because the joint 107 does not have the function to adjust the allowable range of the relative turning angle between the metal column 105 and the metal column 106. This artificial limb joint device using such metal columns is further accompanied by another problem that undesired restrictions are exerted upon the motions between the human body and the joint device because the flexibility which might otherwise be achieved by the protecting members made of a synthetic resin is lost, to induce an abnormal walking manner and to trouble the daily activities.

On the other hand, the artificial limb joint device 111 as shown in FIG. 28, retains the function to adjust the allowable range of the relative turning angle, but this adjustment cannot be accomplished before the joint 118 is removed from the upper protecting member 112 and the lower protecting member 113 to have it parts replaced. In short, the adjustment cannot be attained with the joint device being applied to the human body.

SUMMARY OF THE INVENTION

In order to solve the above-specified problems owned by the aforementioned artificial limb joint device well known in the prior art, therefore, an object of the present invention is to provide an artificial limb joint device which can have its weight reduced by hinging adjoining body protecting members in a manner to turn on an axis perpendicular to their longitudinal axes.

Another object of the present invention is to provide an artificial limb joint device which can not only adjust the allowable range of the relative turning angle between the adjoining protecting members easily, continuously and finely while it is worn on a human body but also fix the allowable range of the turning angle and which can hinge the body protecting members in the manner to turn relative to each other without deteriorating the flexibility of the protecting members.

A further object of the present invention is to provide an artificial limb joint device in which the flexibility of the protecting members can prevent the motions between the joint device and the human body from being undesirably limited, unlike the joint device of the prior art using the metal columns, to induce the abnormal walking and trouble the daily activities.

In order to achieve the above-specified objects, according to the present invention, there is provided an artificial limb joint device for hinging adjoining body protecting members to turn on an axis perpendicular to the longitudinal axes of the body protecting members, comprising: a drive disc; a driven disc; a joint pin extending through the individual centers of the drive disc and the driven disc, the drive disc being detachably attached to one of the adjoining body protecting members and including an outer flange, and an inner flange disposed radially inside of the outer flange and defining an annular groove in the end face of the drive disc together with the outer flange, the outer flange being formed with a through hole extending in a tangential direction of the annular groove, the driven disc being detachably attached to the other of the body protecting members and formed with such a raised segment at the end face confronting the drive disc as to engage in a sliding manner with the annular groove of the drive disc; and a turning motion regulating pin inserted into the through hole to come into and out of the annular groove, for regulating the turning motions of the raised segment in the annular groove.

In the aforementioned artificial limb joint device, the through hole formed in the outer flange of the drive disc may preferably be internally threaded, and the turning motion regulating pin may preferably be so externally threaded as to be driven into the threaded through hole.

Said through hole may be formed in only one portion of the outer flange of the drive disc, and the turning motion regulating pin may be inserted into the through hole. Said through hole may be formed in two portions of the outer flange of the drive disc, and the turning motion regulating pin may be inserted into each of the two through holes.

A turning motion regulating block member may be fitted in the annular groove of the drive disc for regulating the turning motions of the raised segment of the driven disc in the annular groove. Said turning motion regulating pin disposed in the drive disc may be inserted from the through hole of the outer flange through the turning motion regulating block member to come into and out of the annular groove.

A compression spring may be mounted in such a space between the turning motion regulating pin or the turning motion regulating block member of the drive disc and the raised segment of the driven disc as is formed in the annular groove of the drive disc when the drive disc and the driven disc are assembled. A tension spring may also be mounted in such a space between the turning motion regulating pin or the turning motion regulating block member of the drive disc and the raised segment of the driven disc as is formed in the annular groove of the drive disc when the drive disc and the driven disc are assembled, and the tension spring has its one end connected to the turning motion regulating pin or the turning motion regulating block member and its other end connected to the raised segment.

In addition to the turning motion regulating pin and the turning motion regulating block member, a turning motion regulating pin may be inserted radially of the drive disc from a through hole, which is formed in the portion of the outer flange in the annular groove of the drive disc, and into a hole which is formed in the corresponding portion of the inner flange. In this case, the hole for receiving the turning motion regulating pin in the radial direction may be formed in a plurality of portions of the outer and inner flanges of the annular groove of the drive disc. Moreover, the turning motion regulating pins to be inserted radially of the drive disc may be turning motion fixing pins for fixing the turning motions of the raised segment of the driven disc between the tangential turning motion regulating pin and the turning motion regulating block member. Moreover, the raised segment of the driven disc may be formed with a radial through hole so that the turning motion fixing pin can be inserted from the through hole, which is formed in the outer flange portion of the annular groove of the drive disc, and through the through hole, which is formed in the raised segment, into the hole which is formed in the inner flange portion of the annular groove.

In case the aforementioned joint is to be attached to the adjoining body protecting members of the artificial limb joint device, the drive disc and the driven disc may be formed in their individual outer end faces with threaded holes for mounting the body protecting members. Alternatively, the drive disc and the driven disc may be individually formed with connectors extending therefrom for mounting the body protecting members.

In the present joint assembled by bringing the raised segment of the driven disc into sliding engagement with the annular groove of the drive disc, the driven disc may be formed on the inner side of the raised segment with an annular land engaging with the inner face of the inner flange of the annular land of the drive disc.

Moreover, one of the adjoining body protecting members is attached to the drive disc whereas the other of the body protecting members is attached to the driven disc, and the body protecting members are made flexible of a synthetic resin. Furthermore, reinforcing piano wires may be buried or anchored in the body protecting members and fixed to the drive disc and the driven disc.

Since the artificial limb joint device according to the present invention is constructed, as described above, the drive disc and the driven disc assembled with each other are turned on the pin extending therethrough relative to each other, while the raised segment of the driven disc is sliding in the annular groove of the drive disc, with the raised segment being in engagement with the annular groove, so that the body protecting members attached thereto can turn relative to each other. At this turning time, moreover, the turning motions of the raised segment of the driven disc in the annular groove are restricted by the abutment of the raised segment against the turning motion regulating pin which comes tangentially into and out of the annular groove, so that the relative turning motions of the two discs and accordingly the adjoining body protecting members attached to the former are regulated. By adjusting the degree of insertion of the turning motion regulating pin to properly change the protrusion of the same into the annular groove, moreover, the allowable range of the relative turning angle can be continuously adjusted.

If the through hole of the outer flange of the drive disc is threaded and if the turning motion regulating pin is exemplified by a threaded pin, the protrusion of the turning motion regulating pin into the annular groove, i.e., the allowable range of the relative turning angle of the adjoining protecting members may preferably be adjusted more finely and reliably.

In case the turning motion regulating pin is provided in one portion, the relative turning angle is restricted only in one direction, and the allowable range of the turning angle in that direction can be adjusted. On the other hand, in case the turning motion regulating pin is provided in two portions, the relative turning angle is restricted in the two directions, and the allowable ranges of the turning angle in the two directions can be adjusted. The turning motions can be fixed by clamping the raised segment between the two turning motion regulating pins.

In case the turning motion regulating block is disposed in the annular groove in addition to the turning motion regulating pin, the turning motions are regulated in one direction by the turning motion regulating pin while the turning angle allowable range being adjustable, and the turning motion in the other direction is regulated by the turning motion regulating block.

In case the turning motion regulating pin of the drive disc is inserted through the turning motion regulating block member, it is held and reinforced by the block member. Moreover, when the turning motion regulating pin is retracted into the block member, this block member regulates the turning motions of the raised segment of the driven disc.

If the compression spring or the tension spring is arranged in the space between the turning motion regulating pin or block member in the annular groove of the drive disc and the raised segment of the driven disc, the repulsion or tension of the spring is caused to act as a power source for aiding the turning motions of the adjoining protecting members to improve the functions of the artificial limb joint device and promote the remedying effects.

In case the drive disc is equipped with the turning motion regulating radial pin in addition to the aforementioned turning motion regulating and block member, the turning motions of the raised segment can also be regulated and fixed by the added turning motion regulating pin. If, in this case, radial pin can be inserted into a plurality of portions, the allowable range of the turning motions of the raised segment can be adjusted in each of the portions by changing the insertion positions of the pin. If, moreover, the turning motion regulating radial pin is inserted through the raised segment, it can fix the turning motions of the raised segment by itself thereby to fix the relative turning motions between the drive disc and the driven disc by the single action.

By forming the drive disc and driven disc of the joint with threaded holes for mounting the body protecting members, the two adjoining protecting members of the artificial limb joint device can be hinged in a relatively turning manner to each other through the joint by attaching the protecting members in overlapped positions individually to the discs. With the connectors for mounting the body protecting members, these protecting members may be fixed to the connectors by means of screws. Then, the connectors act as members for reinforcing the protecting members.

If, moreover, the raised segment of the driven disc is formed in its inner side with an annular land to engage with the inner face of the inner flange of the drive disc, the joint can have its durability increased to smoothen the relative turning motions better between the drive disc and the driven disc.

Moreover, in the artificial limb joint device according to the present invention wherein the body protecting members made of a flexible material such as a synthetic resin are attached to the joint described above, the two protecting members are connected exclusively by the joint. As a result, the protecting members are prevented from having their flexibility deteriorated unlike the case, in which the metal columns are combined, so that no undesired restriction is exerted upon the motions between the joint device and the human body. Nor is induced any abnormal walking not to trouble the daily activities.

If the piano wires are buried in or anchored at the protecting members of the joint device and are fixed on the drive disc and driven disc of the joint, it is possible to augment the strength and flexibility of the protecting members and to increase the mounting strength between the protecting members and the drive disc and driven disc of the joint.

DESCRIPTION OF THE PREFERRED EMBODIMENTS

The present invention will be described in more detail in the following in connection with the embodiments thereof with reference to the accompanying drawings.

Figure 1:
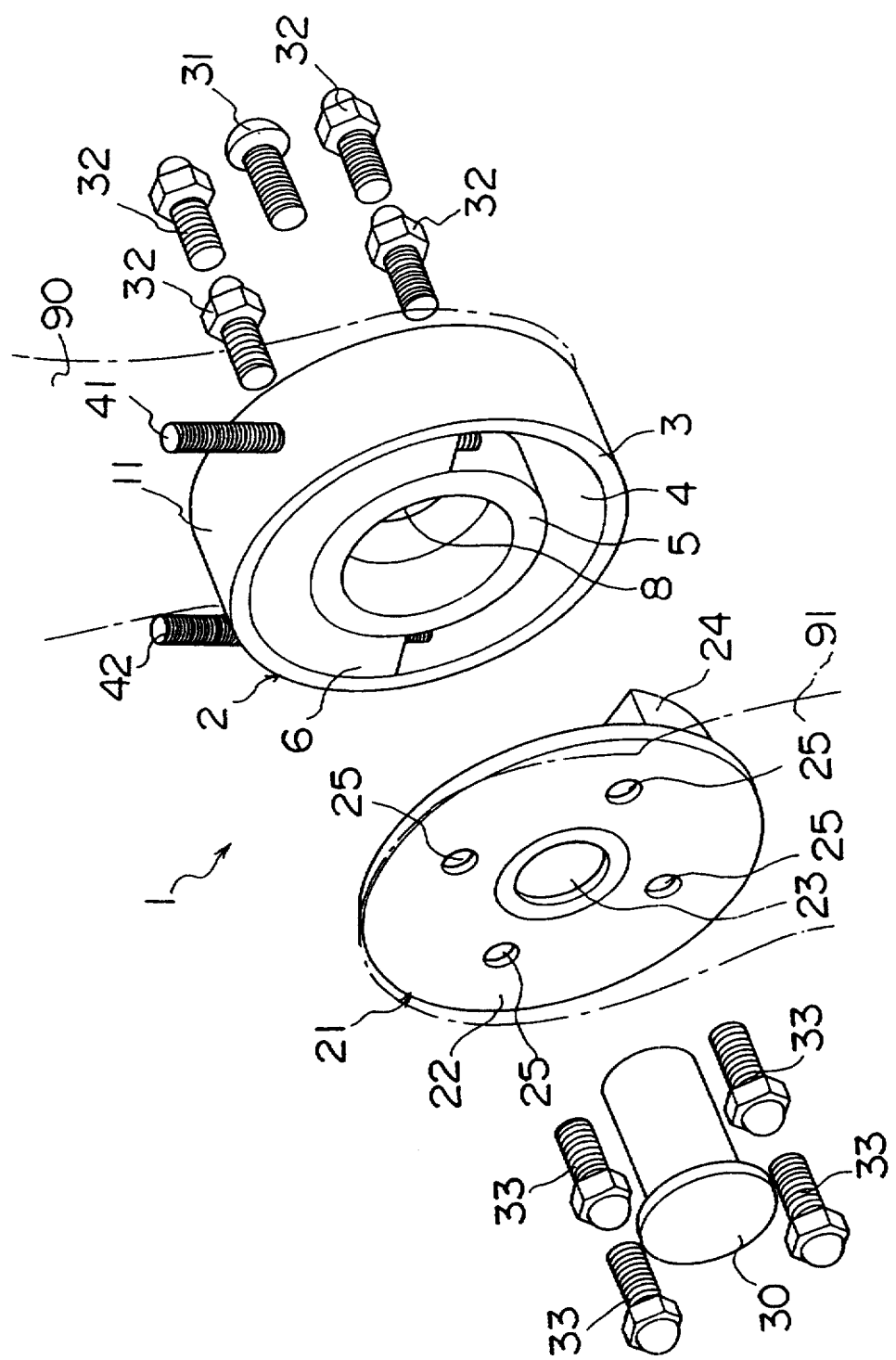
FIG. 1 is an exploded perspective view showing one embodiment of an artificial limb joint device having its turning motions regulated by two threaded pins in accordance with the present invention.

FIG. 1 is an exploded perspective view showing one embodiment of an artificial limb joint 1 according to the present invention.

This joint 1 is constructed to include a drive disc 2, a driven disc 21 and a joint pin 30 extending through the individual centers of the drive disc 2 and the driven disc 21. The drive disc 2 is fixed on one body protecting member 90 by means of four mounting screws 32, and the driven disc 21 is likewise fixed on the other body protecting member 91 by means of four mounting screws 33. The drive disc 2 and the driven disc 21 have their corresponding end faces 13 and 22 formed respectively with threaded holes 12 and 25 which are arranged equidistantly in the circumferential directions.

Thus, the joint 1 can be easily attached to and detached from the protecting members 90 and 91 by using those mounting screws 32 and 33.

Figure 2A:
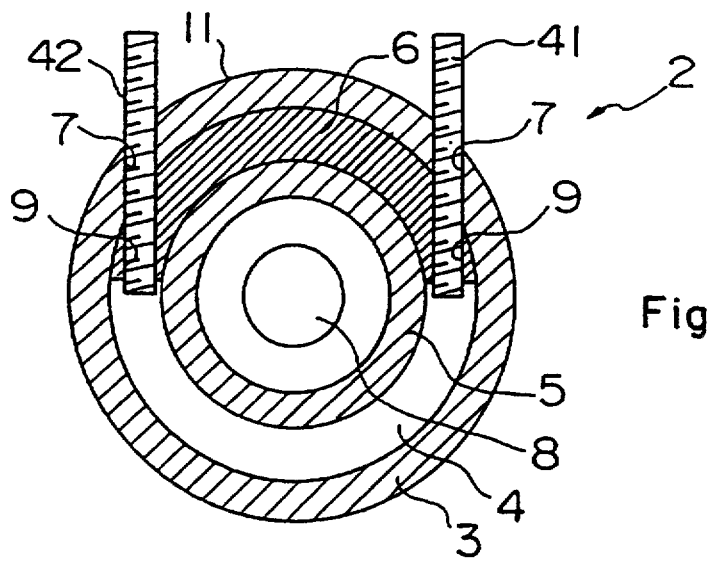
FIG. 2 shows a movable disc in the joint device shown in FIG. 1 and presents at (A) a longitudinally sectional side elevation as taken from a driven disc, at (B) a side elevation as taken from a body protecting member, and at (C) a top plan view.
Figure 2B:
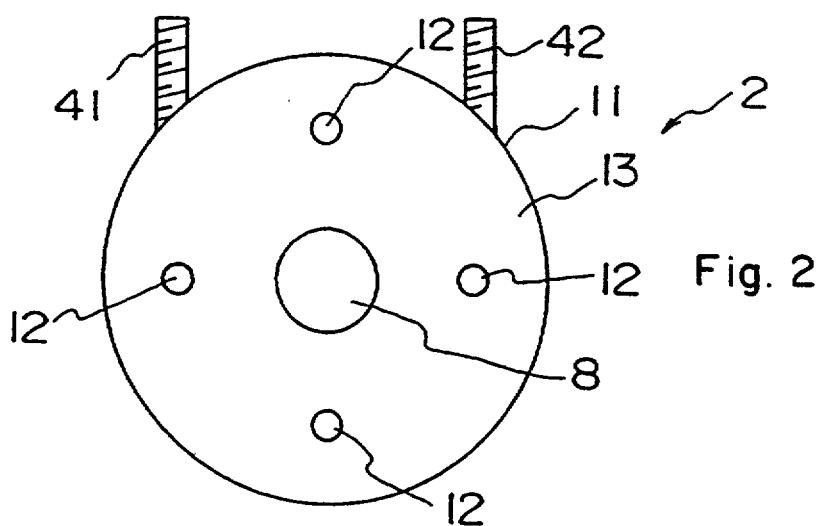
Figure 2C:
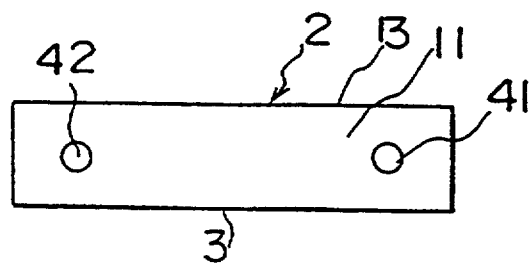

The drive disc 2 is formed, as shown in FIG. 2, with an axial hole 8 at its center and with an inner flange 5, an annular groove 4 and an outer flange 3 outward in radial directions. Moreover, a turn regulating block member 6 is fitted in the upper half of the annular groove 4. The outer flange 3 has its outer circumference 11 formed across the axial hole 8 with threaded holes 7 and 7 which extend in the tangential direction of the annular groove 4. The block member 6 is also formed with threaded holes 9 and 9 which merge into the threaded holes 7 and 7 of the outer flange 3 and extend into the annular groove 4. Through the individual threaded holes 7 and 9, there are so driven two turning motion regulating threaded pins 41 and 42 that they can protrude from the threaded holes 9 of the block member 6 into the annular groove 4.

Figure 3A:
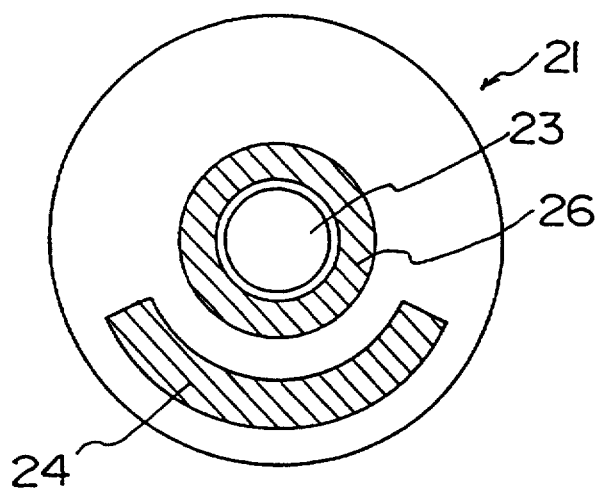
FIG. 3 shows the driven disc in the joint device shown in FIG. 1 and presents at (A) a longitudinally sectional side elevation as taken from the movable disc, at (B) a side elevation as taken from the body protecting member, and at (C) a front elevation.
Figure 3B:
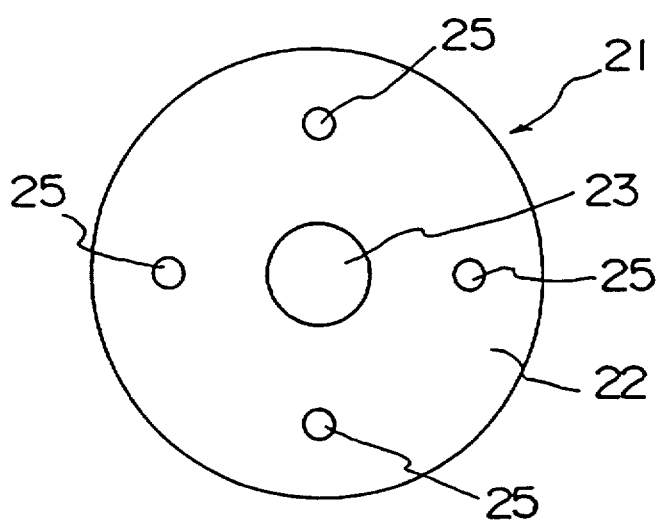
Figure 3C:
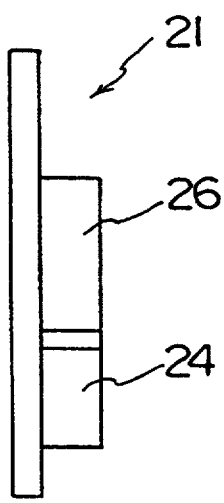

As shown in FIG. 3, on the other hand, the driven disc 21 is formed with an axial hole 23 at its center and with an annular land 26 and a raised segment 24 outward in the radial directions. The annular land 26 is formed to engage in a sliding manner with the inner face of the inner flange 5 of the drive disc 2, and the raised segment 24 is also formed to engage in a sliding manner with the annular groove 4 of the drive disc 2. In this case, it is not the essential structural requisite for the joint device of the present invention that the annular land 26 of the driven disc 21 can engage with the inner face of the inner flange 5 of the drive disc 2. However, this structure is preferred for improving the durability against the stress applied to the joint 1, in case the artificial limb joint device using the joint 1 of the present invention is applied to a human body.

The joint 1 of the present invention, as shown in FIGS. 1 to 3. is assembled in the following manner.

First of all, the individual body protecting members 90 and 91 are attached to the drive disc 2 and the driven disc 21 by using the mounting screws 32 and 33. After this, the drive disc 2 and the driven disc 21 are assembled such that the annular land 26 of the driven disc 21 comes into engagement with the inner flange 5 of the drive disc 2 and that the raised segment 24 comes into engagement with the annular groove 4. The joint pin 30 is inserted from above the protecting member 91 into the axial hole 23 of the driven disc 21 and the axial hole 8 of the drive disc 2 and has its one end fixed by means of its fastening screw 31. As a result, the protecting members 90 and 91 is enabled to turn on the joint pin 30 by the joint 1.

In the joint 1 thus constructed according to the present invention, the sliding motions of the raised segment 24 of the driven disc 21 in the circumferential direction within the annular groove 4 can be regulated by the threaded pins 41 and 42 protruded into the annular groove 4 of the drive disc 2. By changing the protrusions of the threaded pins 41 and 42 properly, moreover, the allowable range of the turning motions can be adjusted. At the same time, the turning motions of the raised segment 24 can be fixed to fix the turning motions of the joint 1 if the two threaded pins 41 and 42 are driven deep to clamp the raised segment 24 inbetween. On the other hand, the turning motions of the raised segment 24 are regulated by the block member 6 if the two threaded pins 41 and 42 are retracted into the block member 6.

Figure 4:
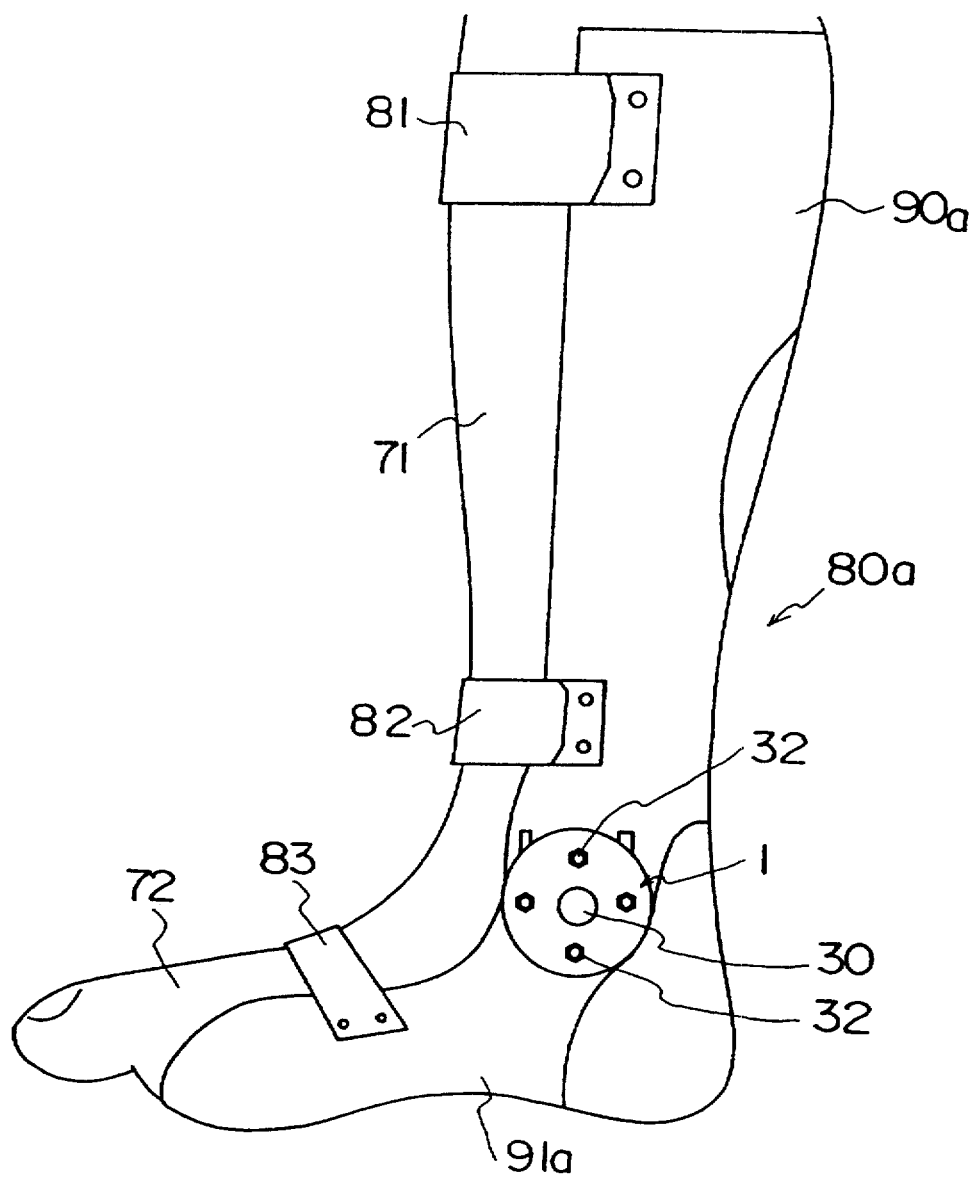
FIG. 4 is a side elevation showing the state in which an artificial ankle joint device using the device of FIG. 1 according to the present invention is applied to a human body.

FIG. 4 shows the state in which an artificial limb joint device 80 using the joint 1 shown in FIGS. 1 to 3 according to the present invention is applied to a human body. The joint device 80 is exemplified by an artificial ankle joint device 80a in which a calf protecting member 90a and a foot protecting member 91a are hinged to each other by the joint 1. The calf protecting member 90a is fixed on a calf 71 by means of two belts 81 and 82, whereas the foot protecting member 91a is fixed on a foot 72 by means of a belt 83. These calf protecting member 90a and foot protecting member 91a are made of a resilient material such as a synthetic resin. Since the protecting members are made of such resilient material, no restriction is exerted upon the relative motions between the calf 71 and the foot 72 so that no abnormal walking motion is induced. Moreover, the drive disc 2 in the joint 1 is fixed to the calf protecting member 90a by the mounting screw 32, whereas the driven disc 21 is fixed to the foot protecting member 91a. At the same time, the joint pin 30 of the joint 1 is inserted together with the two protecting members 90a and 91a through the individual axial holes 8 and 23 of the drive disc 2 and the driven disc 21 so that the calf protecting member 90a and the foot protecting member 91a are jointed rotatably relative to each other by the joint 1.

Figure 5:
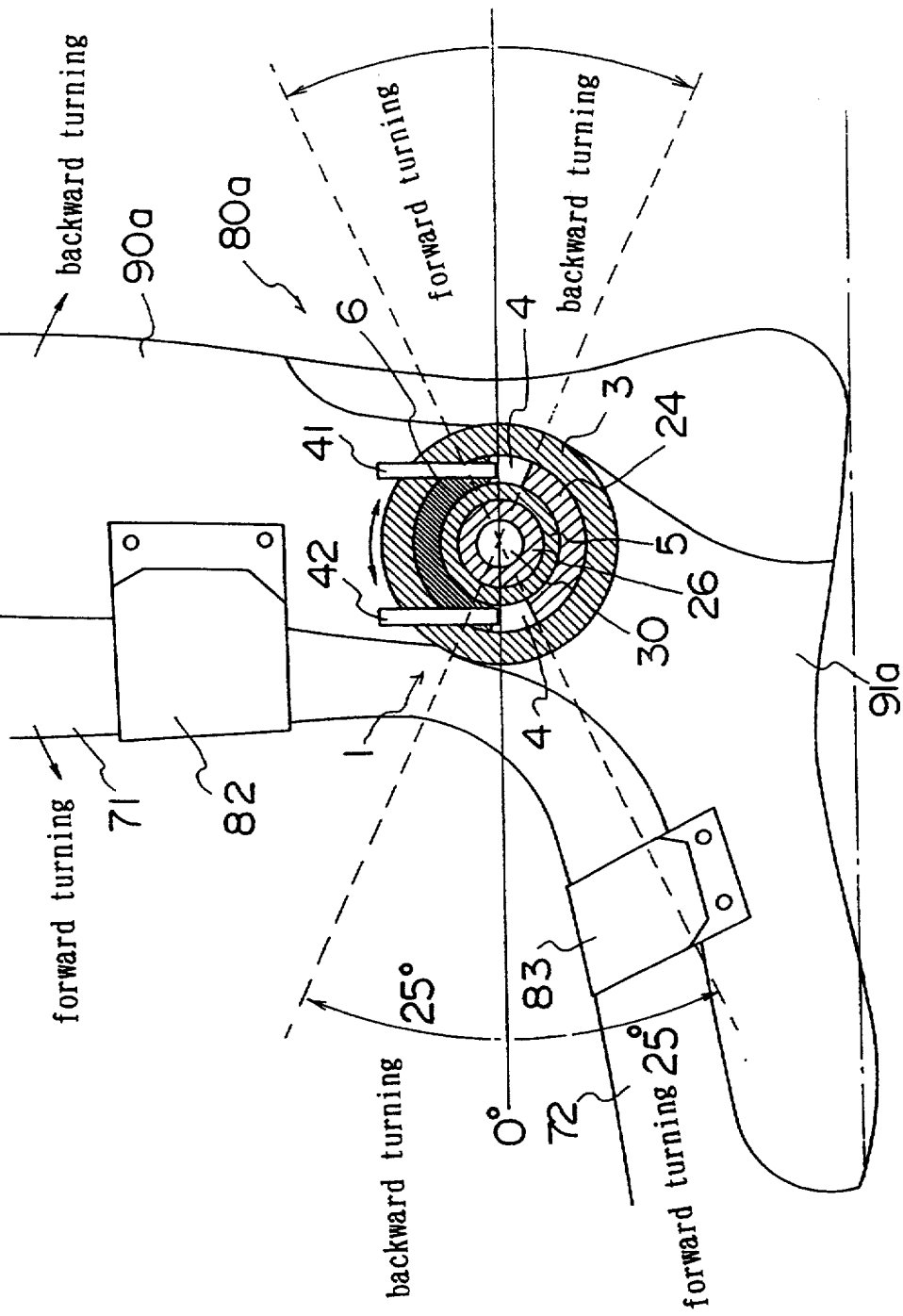
FIG. 5 is a longitudinally sectional side elevation showing an essential portion in case the forward and backward turning angles of the ankle joint in the artificial ankle joint device of FIG. 4 are limited to predetermined values, with a raised segment of the driven disc being fitted in an annular groove of a drive disc, as in the following sections of the joint device.
Figure 6:
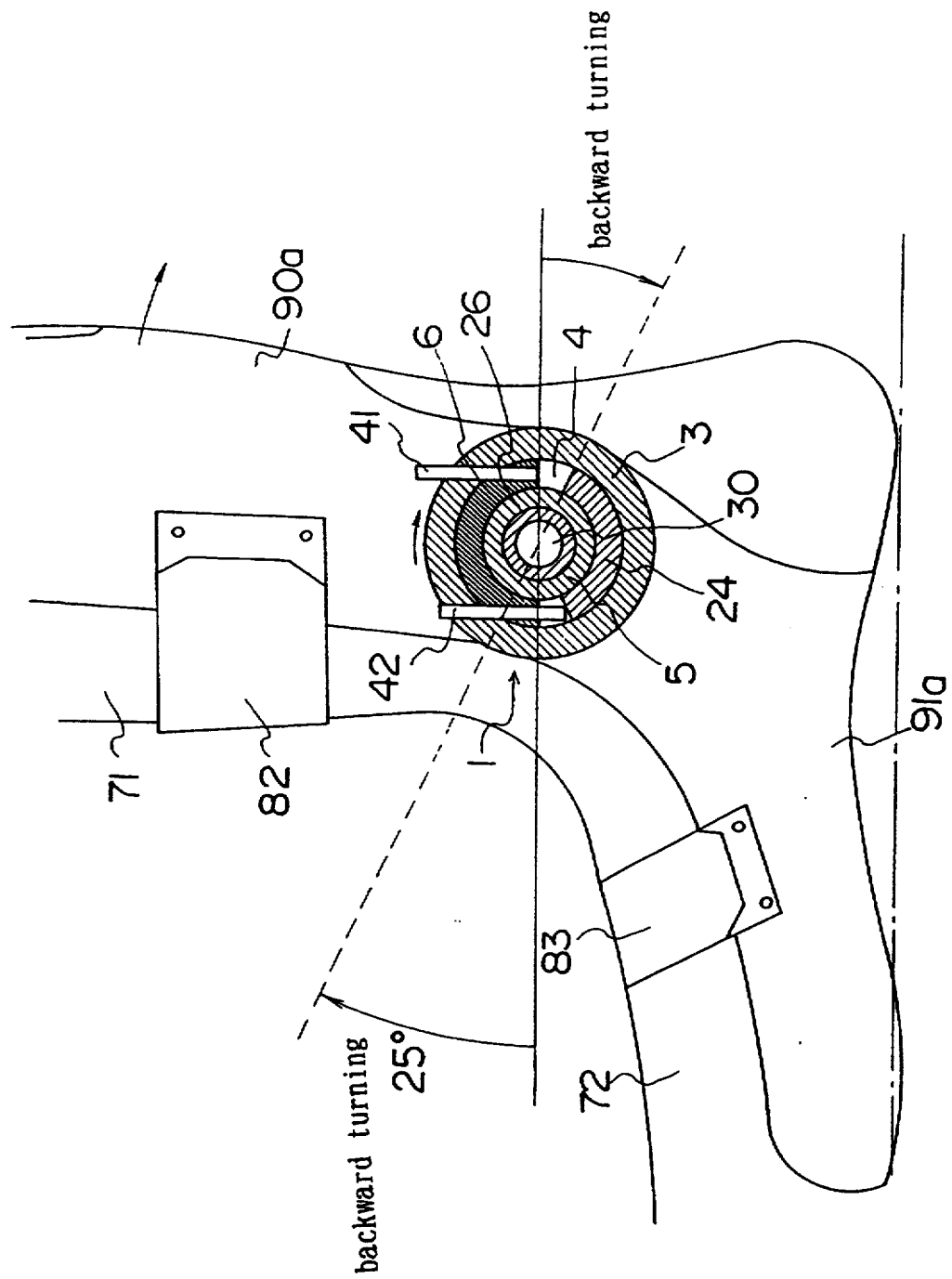
FIG. 6 is a longitudinally sectional side elevation showing an essential portion in case the ankle joint in the artificial ankle joint device of FIG. 4 has its forward turning angle limited to 0 degrees and its backward turning angle limited to a predetermined value.
Figure 7:
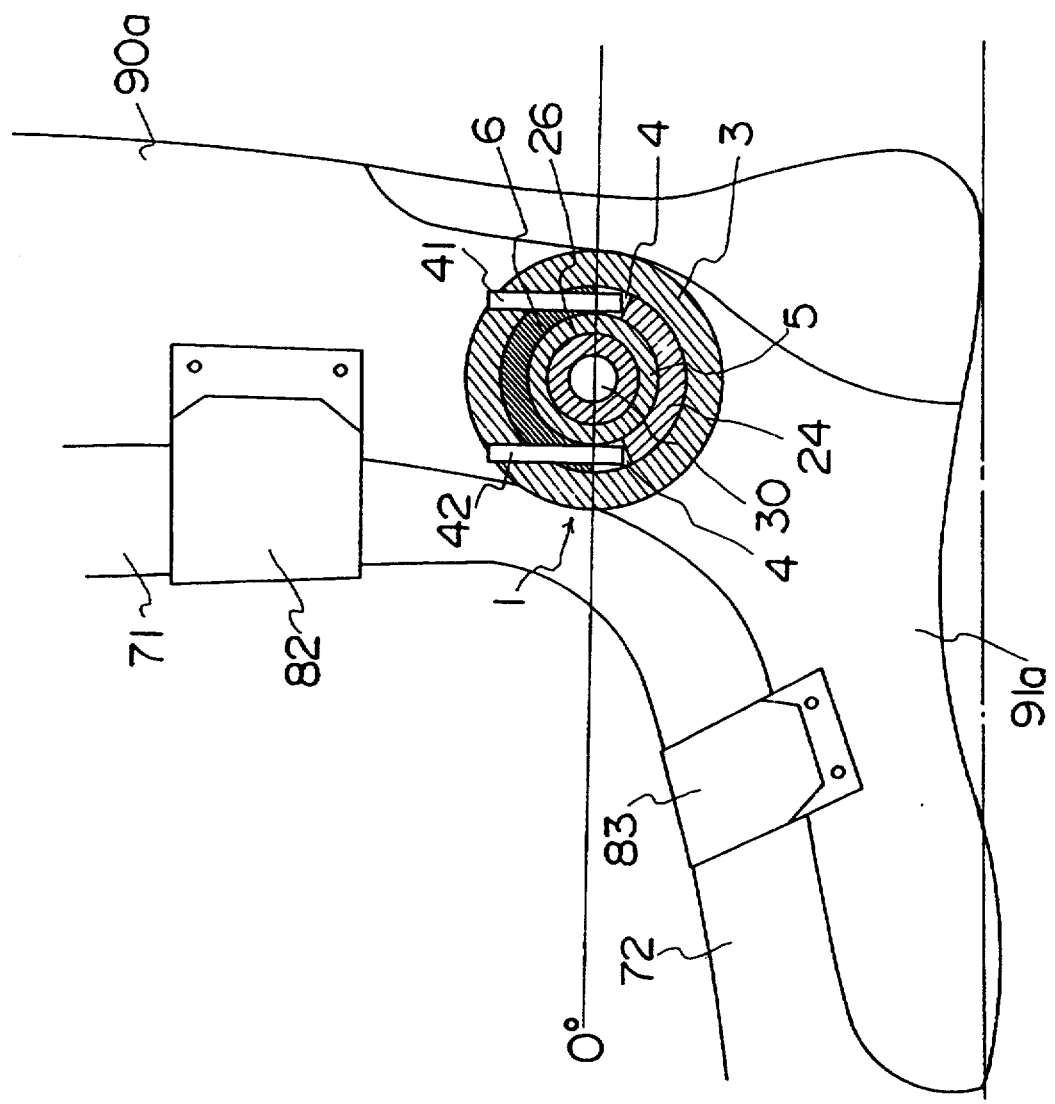
FIG. 7 is a longitudinally sectional side elevation showing an essential portion in case the ankle joint in the artificial ankle joint device of FIG. 4 has both its forward and backward turning angles limited to 0 degrees.

FIGS. 5 to 7 show examples for regulating the turning motions and the turning range of the artificial ankle joint device 80a. FIG. 5 shows the case in which the turning motions at the ankle joint in the forward and backward directions are individually limited within predetermined angular ranges. In this case, the raised segment 24 of the driven disc 21 attached to the foot protecting member 91a is in engagement with the annular groove 4 of the drive disc 2 attached to the calf protecting member 90a. In this state, the drive disc 2 is enabled to turn clockwise and counter-clockwise within a range of 25 degrees relative to the driven disc 21 so that the forward and backward turning motions of the ankle joint are individually limited to 25 degrees. In this case, moreover, the movable range of the ankle joint in the forward and backward directions can be adjusted by changing the driving strokes of the two threaded pins 41 and 42 of the drive disc 2 properly. In case the turn regulating threaded pin 41 at the back side is further driven, for example, the clockwise turning range of the drive disc 2 can be narrowed to make the backward turning angle smaller than 25 degrees. On the other hand, if the turn regulating threaded pin 42 at the front side is further driven, the counter-clockwise turning range of the drive disc 2 can be narrowed to make the forward turning angle smaller than 25 degrees.

FIG. 6 shows the state in which the turning motions in the artificial ankle joint device 80a are further regulated to limit the forward turning motion of the ankle joint to 0 degrees but to adjust the backward turning motion to an angle up to 25 degrees. Specifically, the front threaded pin 42 in the drive disc 2 of the joint 1 is driven to come into abutment against the raised segment 24 of the driven disc 21, and the back threaded pin 41 in the annular groove 4 is so adjusted to form a space of the angle of 25 degrees between it and the raised segment 24 that the drive disc 2 attached to the calf protecting member 90a can turn as far as it comes into abutment against the raised segment 24 of the driven disc 21. Thus, the ankle joint has its forward turning angle restricted to 0 degrees and its backward turning angle allowed to 25 degrees.

FIG. 7 shows the case in which both the forward and backward bending angles of the ankle joint are restricted and fixed to 0 degrees by using the artificial ankle joint device 80a. The relative turning motions between the drive disc 2 and the driven disc 21 are fixed to fix the calf protecting member 90a and the foot protecting member 91a by driving both the two threaded pins 41 and 42 of the drive disc 2 until they come into abutment against the raised segment 24 of the driven disc 21.

In the artificial ankle joint device 80a using the joint 1 according to the present invention, as described above, the driving strokes of the two threaded pins 41 and 42 in the drive disc 2 of the joint 1 can be properly adjusted to change their insertions into the annular groove 4. As a result, the turning range of the raised segment 24 of the driven disc 21 engaging to slide in the annular groove 4 can be adjusted to regulate the forward and backward bending angles of the ankle joint or fix them, if necessary. Moreover, the turn regulating pins need not be the threaded pins but may be any that can adjust the insertions into the annular groove 4 properly. In case, however, the threaded pins are used, it is easy and preferable to adjust the driving strokes continuously and finely.

Figure 8:
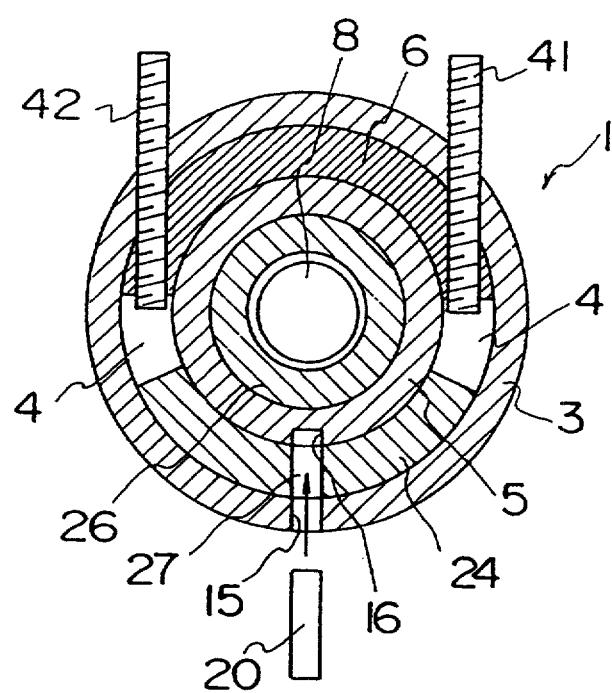
FIG. 8 is a longitudinally sectional side elevation showing an embodiment, in which the joint device of FIG. 1 has its turning motions fixed by driving the threaded pins into holes which are formed in the outer and inner flanges of the drive disc and in the raised segment of the driven disc.

On the other hand, in case the turning motion of the joint 1 is fixed, the outer flange 3 and inner flange 5 of the drive disc 2 can be respectively formed with radial through holes 15 and 16, and the raised segment 24 of the driven disc 21 can be formed with a radial through hole 27, as shown in FIG. 8, for example. Then, if a fixing pin 20 is radially inserted toward the inner flange 5 from the through hole 15 of the outer flange 3 and the through hole 27 of the raised segment 24, the turning motions of the joint 1 can be fixed by the simple operation of single action while eliminating the troublesome actions of driving the threaded pins 41 and 42.

Figure 9:
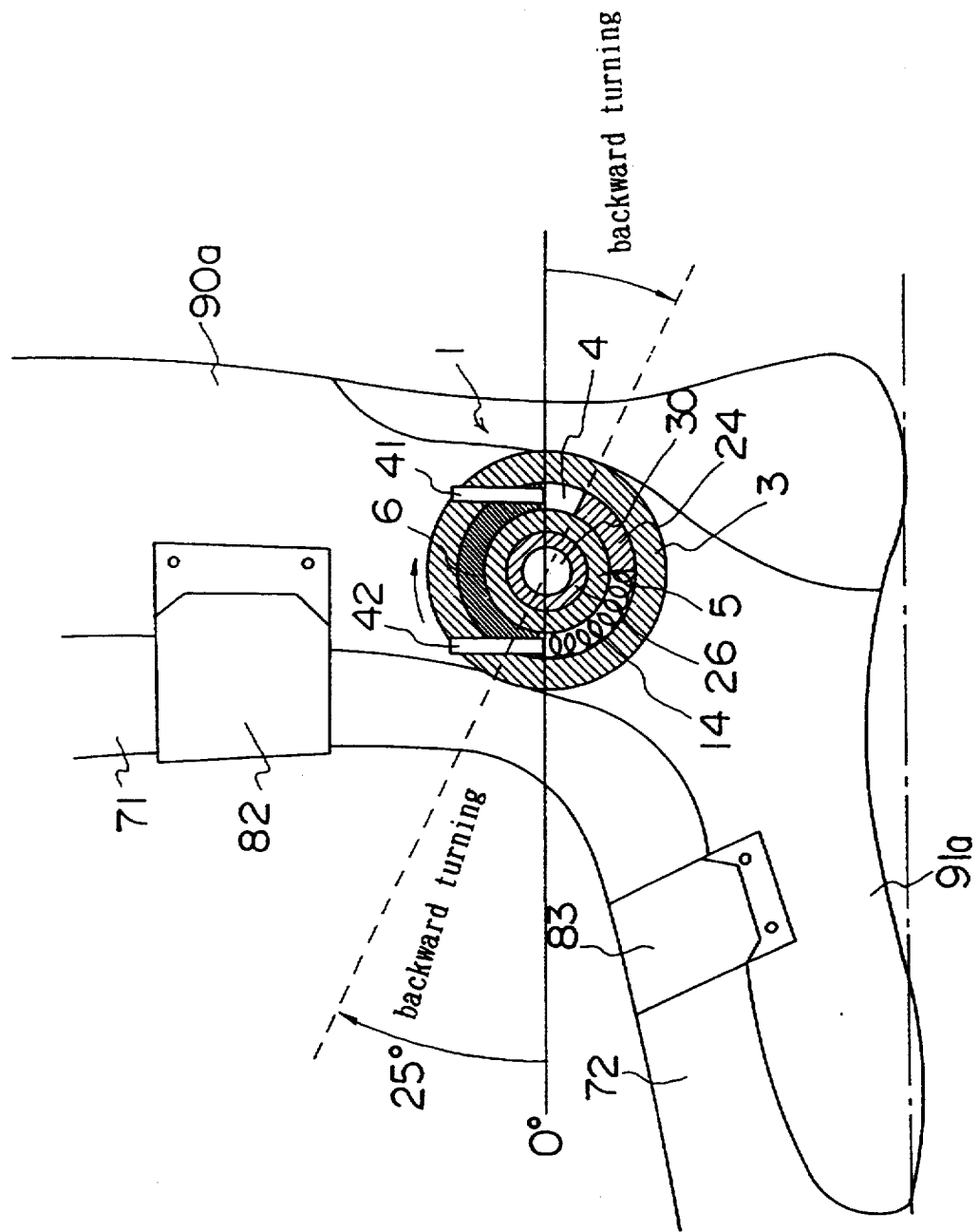
FIG. 9 is a longitudinally sectional side elevation showing an essential portion in case the ankle joint of the ankle joint device of FIG. 4 has its forward turning angle limited to 0 degrees by a compression spring, which is sandwiched between the threaded pin of the drive disc and the raised segment of the driven disc and its backward turning angle limited to a predetermined value while aiding the backward turning motion by the repulsion of the compression spring.

FIG. 9 shows the artificial ankle joint device 80a using another embodiment of the joint 1. In this embodiment, there is mounted between the turning motion regulating threaded pin 42 in the annular groove 4 of the drive disc 2 and the raised segment 24 a spring 14, which is usually exemplified by a compression spring but may be exemplified by a tension spring. Incidentally, this tension spring is required, if used, to have its two ends connected to the threaded pin 42 and the raise segment 24. In the embodiment of FIG. 9 using the spring 14 together, moreover, the forward bending angle is limited to 0 degrees under the compressed state of the spring 14, and the joint 1 can be turned backward within a range of 25 degrees till the threaded pin 41 comes into abutment against the raised segment 24, and the repulsion of the spring 14 acts as a power source for the turning motion to aid the backward bend. By thus using the spring 14 together in the joint 1 according to the present invention, the present artificial ankle joint device 80a is enabled to aid the turning motions of the ankle joint of its user. In this case, moreover, an arbitrary spring force by the spring 14 can be achieved by properly adjusting the driving stroke of the threaded pin 41 anchoring one end of the spring 14 so that the turning range of the joint 1 and the motion aiding power of the spring can be attained independently of the intensity of the power of the spring 14 itself.

Figure 10:
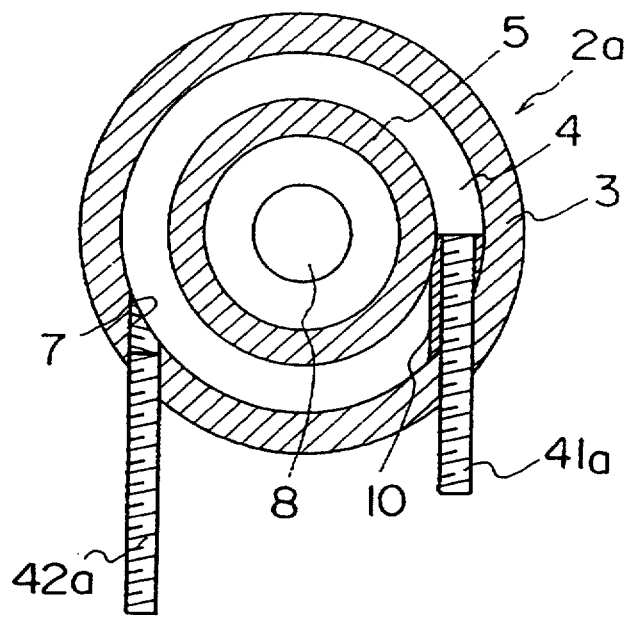
FIG. 10 is a longitudinally sectional side elevation taken from the driven disc and showing a drive disc of an artificial limb joint device which has its turning motions regulated by two threaded pins in accordance with another embodiment of the present invention.
Figure 11:
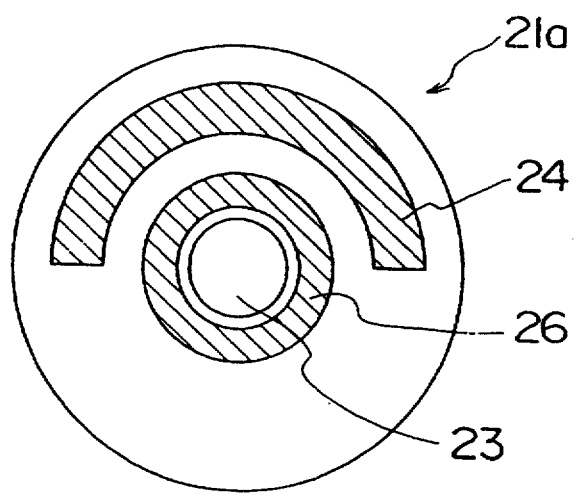
FIG. 11 is a longitudinally sectional side elevation showing a driven disc to be combined with the drive disc shown in FIG. 10, as taken from the drive disc.

FIG. 10 shows a drive disc 2a of still another embodiment of the joint 1 according to the present invention, and FIG. 11 shows a driven disc 21a to be combined with the drive disc 2a of FIG. 10. In the drive disc 2a shown in FIG. 10, two turning motion regulating threaded pins 41a and 42a can be driven into the annular groove 4 from the lower portion of the outer flange 3 but without fitting the turning motion regulating block member in the annular groove 4, and a washer 10 is fitted around the turning motion regulating threaded pin 41a at the back side. On the other hand, the driven disc 21a to be combined with the drive disc 2a of FIG. 10 is formed, as shown in FIG. 11, with the raised segment 24 of a semicircular arc which can engage in a sliding manner with the annular groove 4 of the drive disc 2a. The raised segment 24 is located on the end face confronting the drive disc 2a and outside of the annular land 26 engaging in a sliding manner with the inner face of the inner flange 5 of the drive disc 2a.

Figure 12:
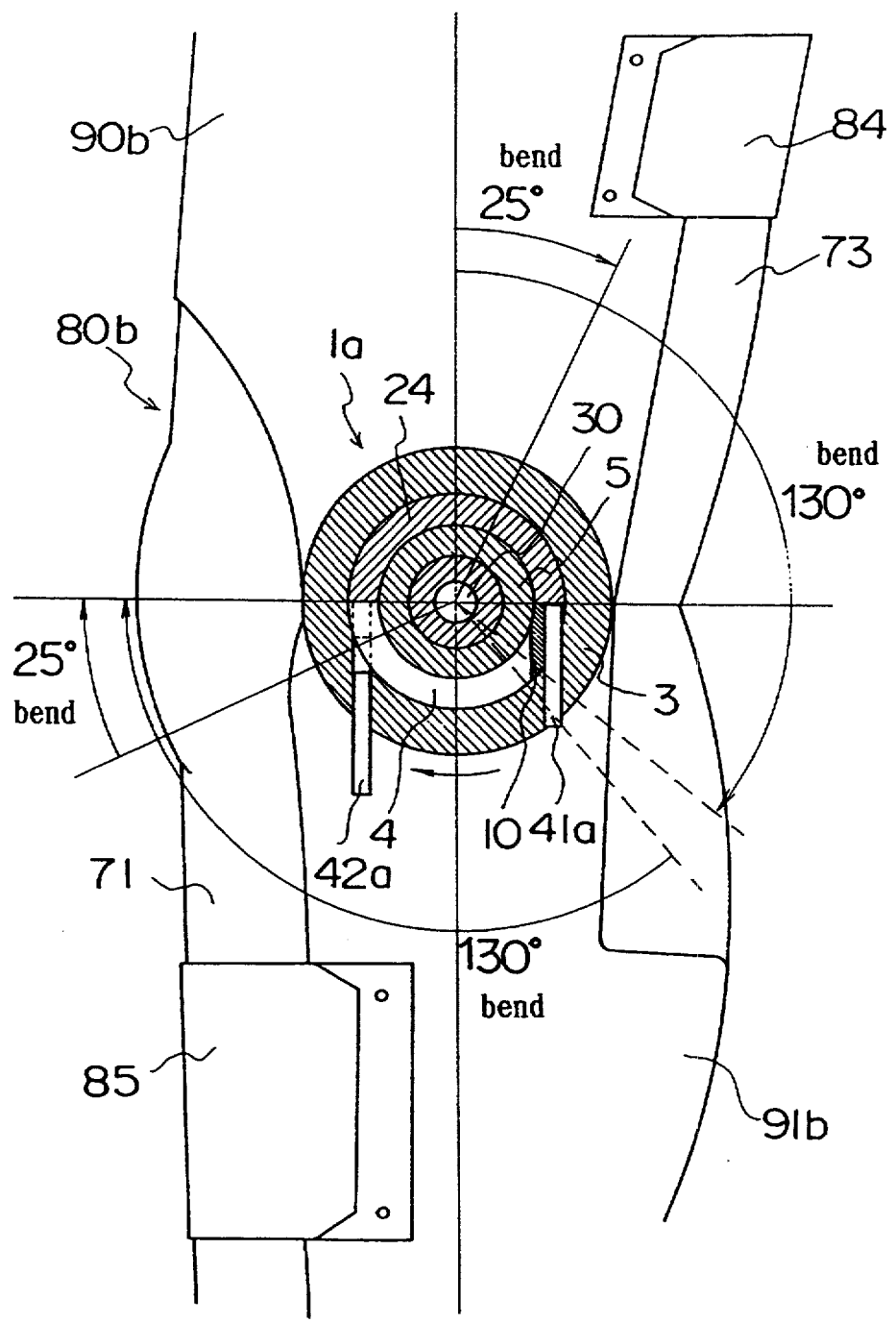
FIG. 12 is a longitudinally sectional side elevation showing an essential portion in case an artificial knee joint device according to the present invention using a joint composed of the drive disc of FIG. 10 and the driven disc of FIG. 11 is applied to a human body.

FIG. 12 shows the state in which an artificial knee joint device 80b using a joint 1a composed of the drive disc 2a and the driven disc 21a, as shown in FIG. 10 and FIG. 11, is applied to a human body. This artificial knee joint device 80b is worn by hinging a thigh protecting member 90b and a calf protecting member 91b by means of the joint 1a. The thigh protecting member 90b is made of a synthetic resin or the like and is fixed on a thigh 73 by means of a belt 84, whereas the calf protecting member 91b is likewise made of a synthetic resin or the like and is fixed on the calf 71 by means of a belt 85. Moreover, the thigh protecting member 90b is attached to the drive disc 2a in the joint 1a, whereas the calf protecting member 91b is attached to a driven disc 21a.

In the joint 1a in the artificial knee joint device 80b shown in FIG. 12, the turning motion regulating threaded pin 41a at the back side of the drive disc 2a can protrude from the washer 10 when it takes a generally horizontal position around the joint pin 30, and the base end of the washer 10 positioned on the inner face of the outer flange 3 is turned by about 130 degrees on the joint pin 30 from a horizontal position which is taken by the end portion of the raised segment 24. On the other hand, the turning motion regulating threaded pin 42a at the front side can protrude directly into the annular groove 4 from the inner face of the outer flange 3 and has its protrusion positioned in the annular groove 4 of the threaded pin 42a and turned about 25 degrees from a horizontal position on the joint pin 30. In the present joint 1a, therefore, the drive disc 2a is allowed to turn only counter-clockwise on the joint 1a with respect to the driven disc 21a and to limit the turning angle of the knee joint to 0 degrees in the extending direction while allowing the knee joint only to bend. Moreover, this bending angle is given the maximum of 25 degrees, in case the threaded pin 42a is protruded into the annular groove 4, till the raised segment 24 of the driven disc 21a turning relative to the drive disc 2a comes into abutment against the threaded pin 42a protruded into the annular groove 4. Still moreover, the turning angular range is narrowed by driving the threaded pin 41a into the annular groove 4. In case, on the other hand, the threaded pin 42a is retracted into the outer flange 3, the drive disc 2a is allowed to turn to bend the knee joint up to 130 degrees till the raised segment 24 of the driven disc 21a turning relative to the drive disc 2a comes into abutment against the washer 10. In the state shown in FIG. 12, moreover, the thread pin 41a at the back side is within the washer 10 but can be properly protruded from the washer 10 to extend the knee joint excessively to the maximum of 25 degrees.

Thus, according to the artificial knee joint device 80b described above, the knee joint can be continuously adjusted from the excessively extended position of 25 degrees to the bent position of 25 degrees by the actions of the two turning motion regulating threaded pins 41a and 42a. Moreover, the bend and extension within the range of 130 degrees can be achieved by retracting the threaded pin 42a. Still moreover, the bent position from 0 degrees to 25 degrees can be continuously adjusted and braked by protruding the threaded pin 42a properly into the annular groove 4. In addition, the turning motion can be fixed by driving the threaded pin 42a until it comes into abutment against the raised segment 24. In this fixing case, furthermore, the turning motion can be fixed over a wide range from the over-extended position of 25 degrees to the bent position of 25 degrees and in an arbitrary position by bringing the threaded pins 42a and 41a at the front and back sides into simultaneous abutment against the raised segment 24 while giving them the corresponding protrusions.

Figure 13:
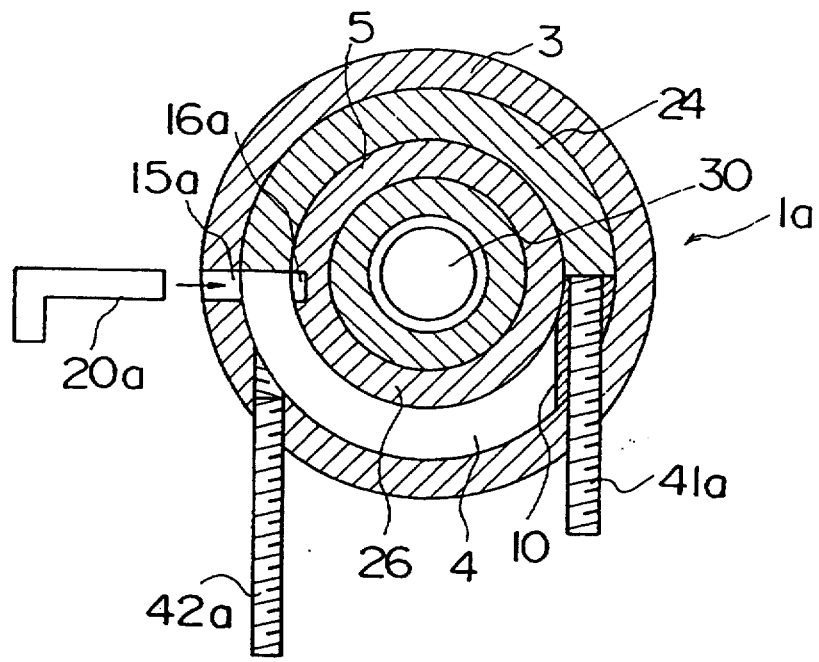
FIG. 13 is a longitudinally sectional side elevation showing an example, in which the joint of the artificial knee joint device shown in FIG. 12 has its turning motions regulated by driving the threaded pins into holes which are formed in the outer and inner flanges of the drive disc.
Figure 14:
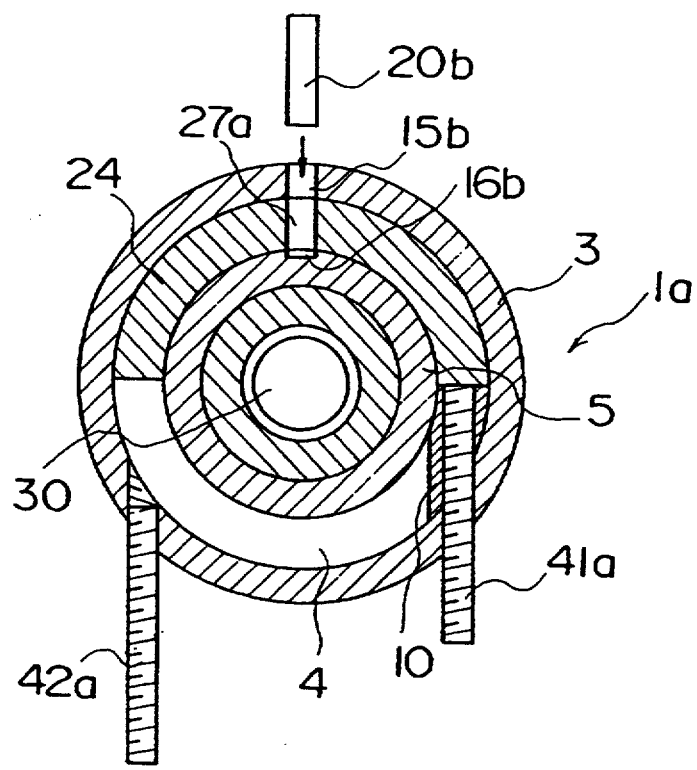
FIG. 14 is a longitudinally sectional side elevation showing an example, in which the joint of the artificial knee joint device shown in FIG. 12 has its turning motions regulated by driving the threaded pins into holes which are formed in the outer and inner flanges of the drive disc and in the raised segment of the driven disc.

FIGS. 13 and 14 show other embodiments of the structure for fixing the turning motions of the joint 1a of the artificial knee joint device 80b shown in FIG. 12. In the embodiment shown in FIG. 13, the outer flange 3 and the inner flange 5 in horizontal positions on the joint pin 30 in the joint 1a are individually formed with radially extending through holes 15a and 16a for inserting a fixing pin so that the turning motions of the raised segment 24 are fixed by inserting a fixing pin 20a into those through holes 15a and 16a. In the embodiment shown in FIG. 14, on the other hand, the raised segment 24 is formed with a fixing pin inserting hole 27a so that its turning motions in the annular groove 4 can be fixed by inserting a fixing pin 20b radially into a hole 16b of the inner flange 5 from a through hole 15b of the outer flange 3 and the through hole 27a of the raised segment 24.

Figure 15:
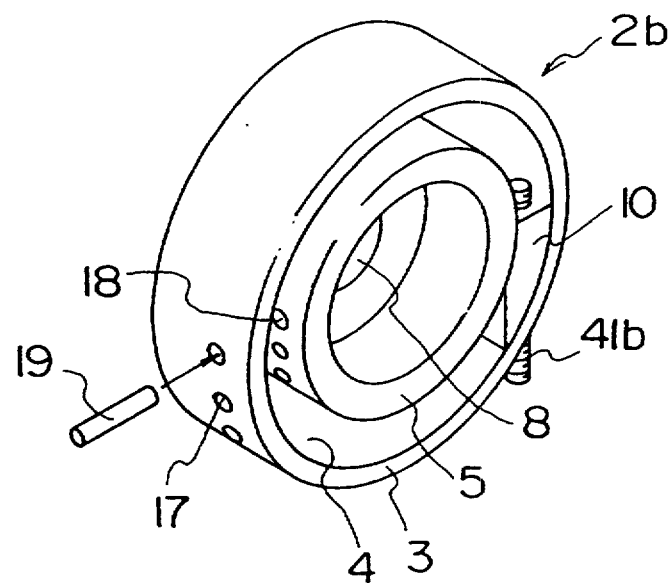
FIG. 15 is a perspective view showing an example, in which the joint of the artificial knee joint device has its turning motions regulated in one direction by a tangential threaded pin and fixed or regulated in another direction by inserting a radial pin into one of a plurality of holes which are formed in the outer and inner flanges of the drive disc.

FIG. 15 shows another embodiment of the drive disc. In this drive disc 2b, the outer flange 3 and the inner flange 5 are formed with a plurality of holes 17 and 18 which are spaced at 15 degrees.

Figure 16:
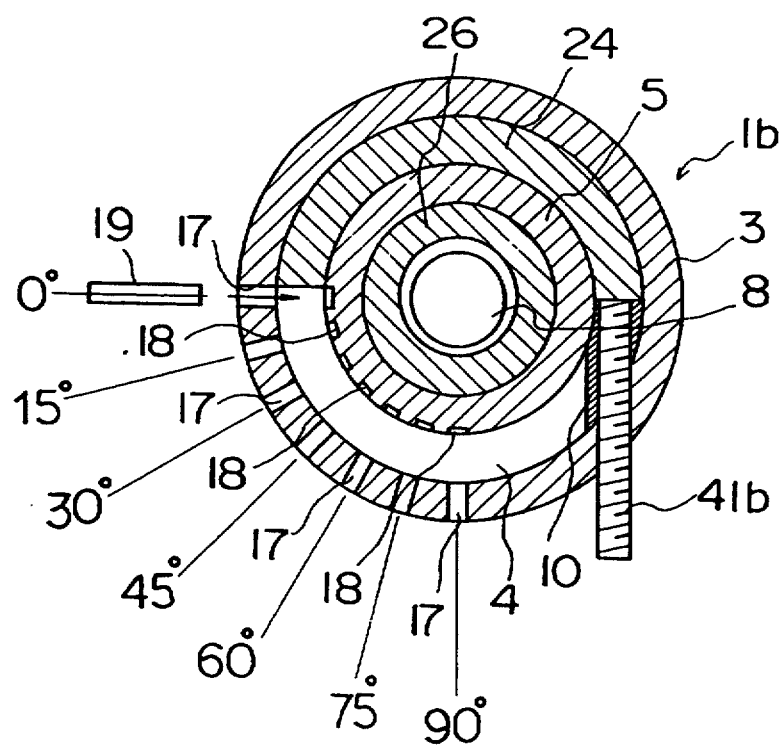
FIG. 16 is a longitudinally sectional side elevation showing a joint using the drive disc of FIG. 15.

A turning motion regulating pin 19 is radially inserted from the through hole 17 of the outer flange 3 into the hole 18 of the inner flange 5 so that the turning motions of the raised segment 24 of the driven disc 21b can be regulated at the interval of 15 degrees by the radial pin 19 when the driven disc 21b is combined with the drive disc 2b, as shown in FIG. 16.

Figure 17:
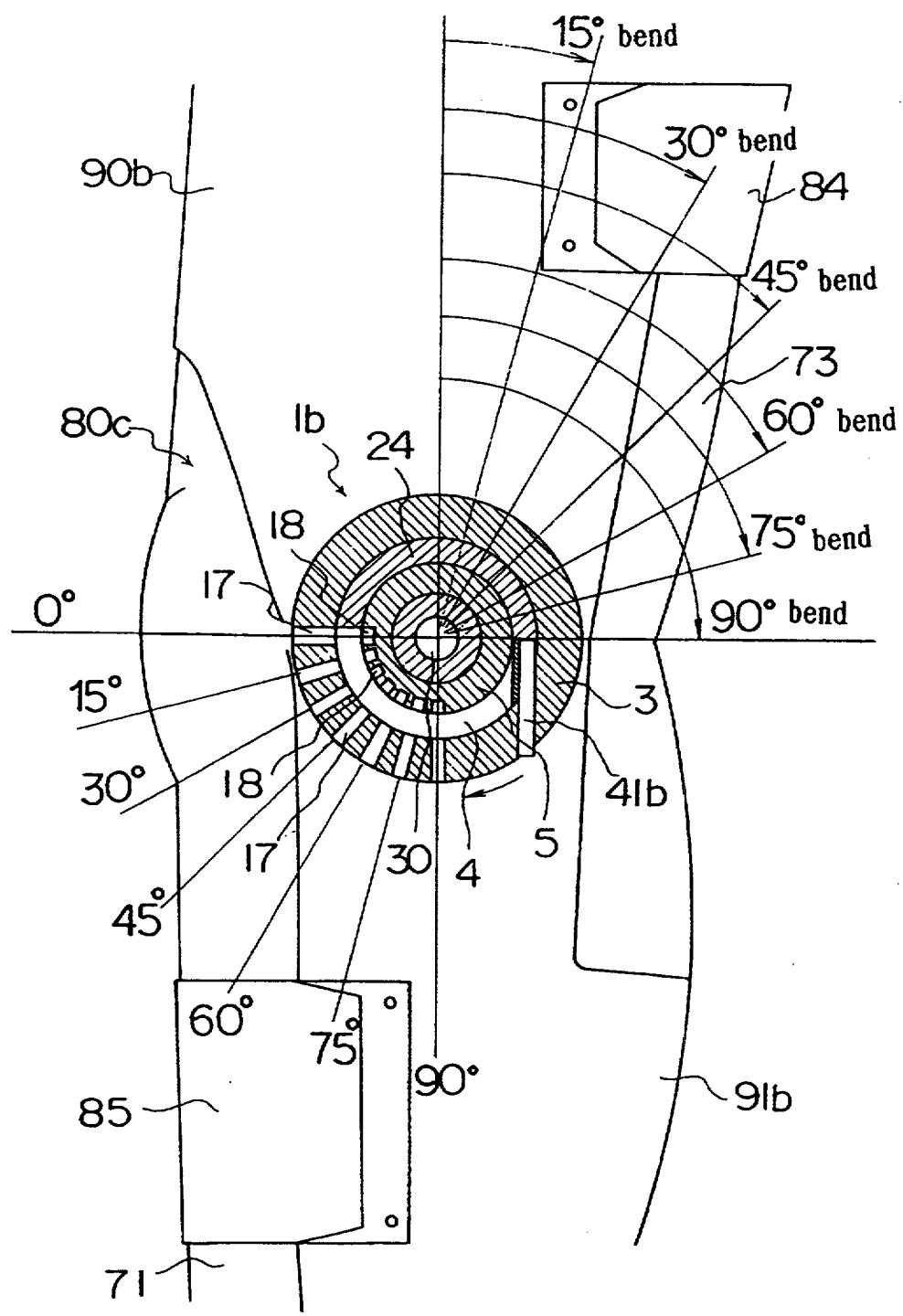
FIG. 17 is a longitudinally sectional side elevation showing an essential portion in case the artificial knee joint device using the joint shown in FIG. 16 is applied to a human body.

FIG. 17 shows an artificial knee joint device 80c using the joint 1b shown in FIG. 15 and FIG. 16. In this knee joint device 80c, the knee joint can be fixed at an extension of 0 degrees or regulated in its turning motions at an interval of 15 degrees from the fixed position of 0 degrees to a bent position of 90 degrees by inserting the turning motion regulating radial pin 19 into arbitrary one of the pin holes 17 and 18 which are formed in the circumference of the joint 1b. At the same time, the knee joint can be continuously and finely fixed in an over-extended position up to about 25 degrees by adjusting a turning motion regulating tangential threaded pin 41b driven in the joint 1b.

Figure 18:
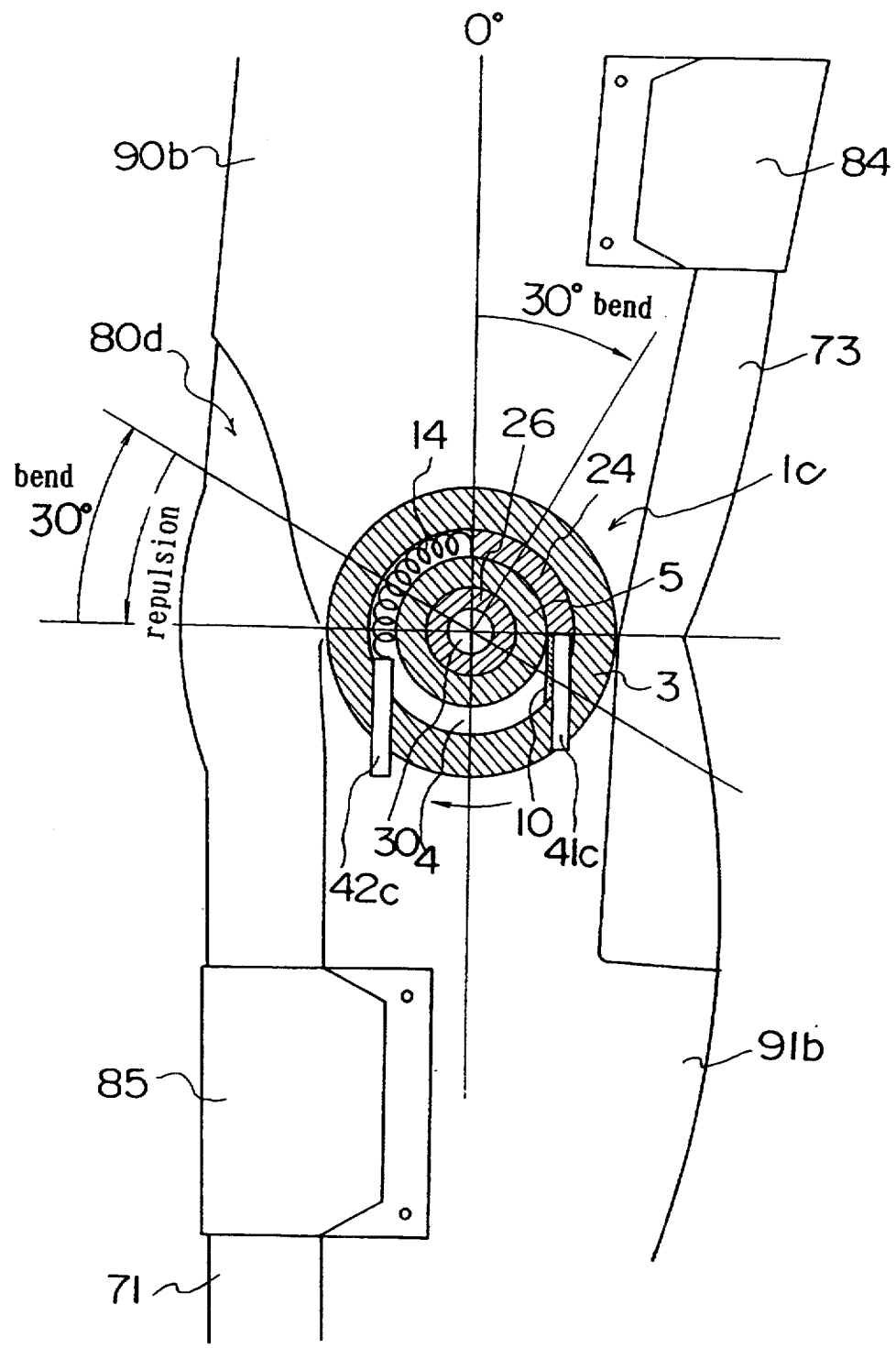
FIG. 18 is a longitudinally sectional side elevation showing an essential portion of an embodiment, in which there is applied to a human body an artificial knee joint device having its knee joint extension aided by a compression spring and limited to 0 degrees.
Figure 19:
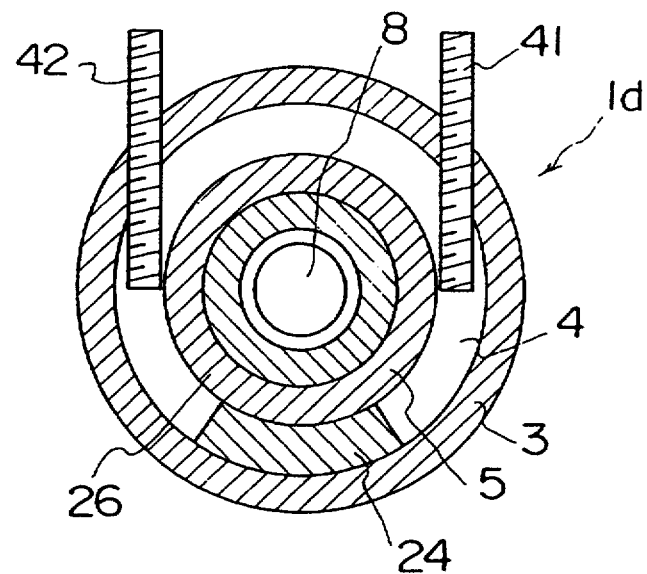
FIG. 19 is a longitudinally sectional side elevation of the drive disc, as taken from the driven disc, and shows another embodiment of an artificial limb joint device having its turning motions restricted in two directions by two threaded pins in accordance with the present invention.
Figure 20:
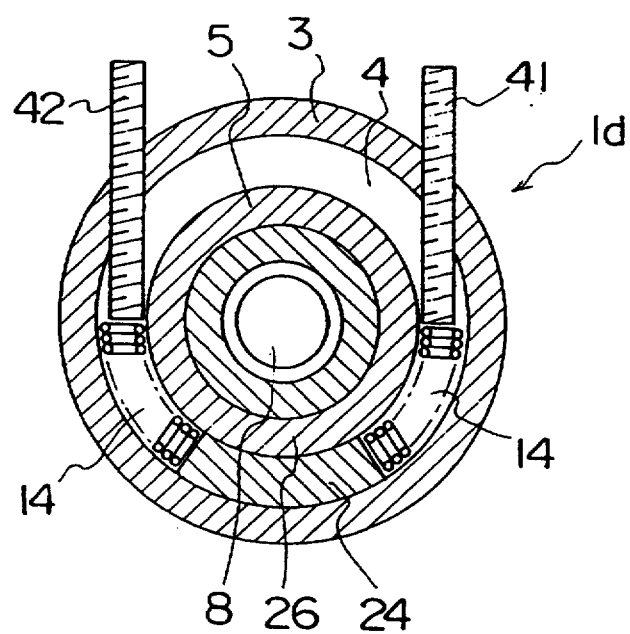
FIG. 20 is a longitudinally sectional side elevation showing an embodiment, in which the joint using the drive disc shown in FIG. 19 has its turning motions aided or restricted in one or two directions by springs.
Figure 21:
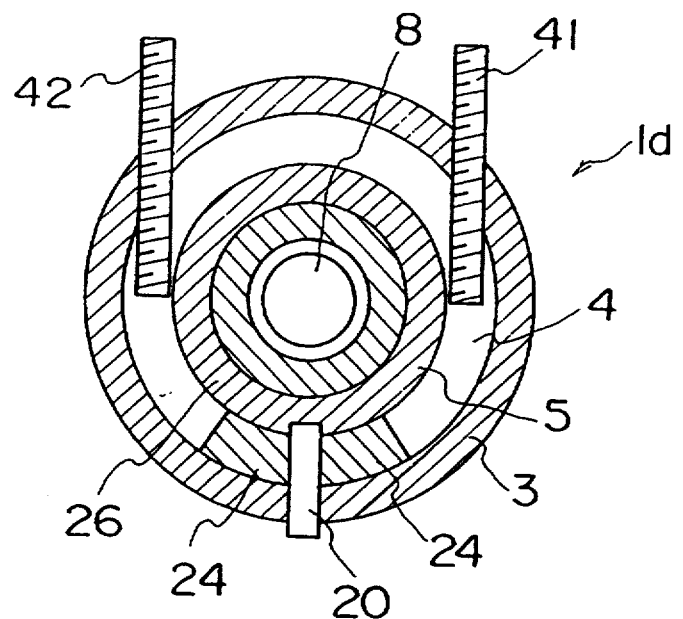
FIG. 21 is a longitudinally sectional side elevation showing an embodiment, in which the joint shown in FIG. 20 has its turning motions fixed by inserting pins into holes which are formed in the outer and inner flanges of the drive disc and in the raised segment of the driven disc.
Figure 22:
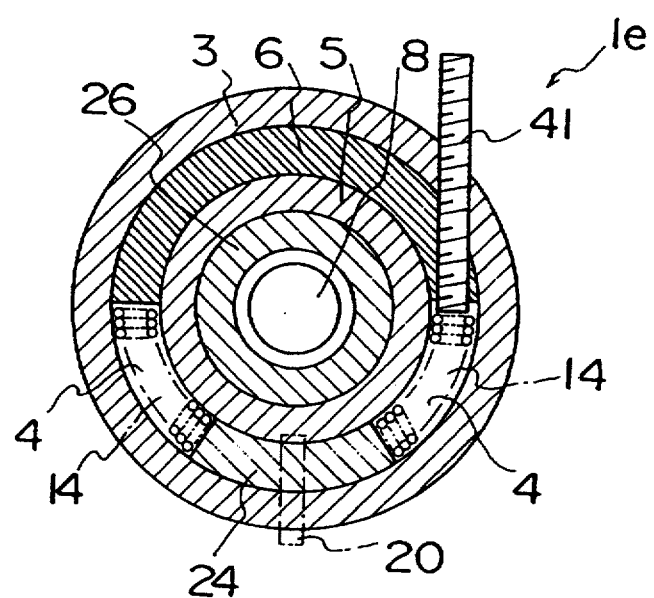
FIG. 22 is a longitudinally sectional side elevation showing still another embodiment of the artificial limb joint device according to the present invention, in which the turning motion is regulated in one direction by a threaded pin and in another by a block.

FIG. 18 shows a further embodiment of the artificial knee joint device. In this knee joint device 80d, a drive disc 2c of a joint 1c is equipped with two turning motion regulating threaded pins 41c and 42c, and a spring 14 is mounted between the one threaded pin 42c and the raised segment 24 of a driven disc 21c. The knee joint has its extension limited to 0 degrees by the other threaded pin 41c. At the same time, the knee joint can be bent up to 30 degrees and can have its extension aided by the spring 14 between the threaded pin 42c and the raised segment 24. In this case, too, the knee joint can be fixed in an over-extended position at a proper angle by adjusting the threaded pin 41c, and the bent angle is adjusted by the other threaded pin 42c. In addition, the force of the spring 14 can be changed by adjusting those threaded pins 41c and 42c.

FIGS. 19 to 22 show other embodiments of the joint according to the present invention. In the joint 1d shown in FIG. 19, the two turning motion regulating threaded pins 41 and 42 are tangentially driven into and output the annular groove 4 directly from the inner face of the outer flange 3 of the drive disc 2. The moving range of the raised segment 24 of the driven disc 21 can be adjusted by adjusting the two threaded pins 41 and 42. In case one of these threaded pins 41 and 42 is either retracted into the outer flange 3 or removed, the moving angular range of the raised segment 24 can be increased in that direction. In case, moreover, both of them are retracted from the annular groove 4, turning motions of 360 degrees can be achieved. In the embodiment shown in FIG. 20, the turning motions of the joint 1d are aided by mounting the spring 14 either between the one threaded pin 41 of the joint 1d of FIG. 19 and the raised segment 24 or additionally between the other threaded pin 42 and the raised segment 24. In this case, too, the moving angular range and the force of the spring 14 can be changed by adjusting the two threaded pins 41 and 42. In the embodiment shown in FIG. 21, on the other hand, the turning motion fixing radial pin 20 can be inserted into the joint 1d shown in FIG. 19, to fix the turning motions of the joint 1d by a single action. In the embodiment shown in FIG. 22, on the other hand, a joint 1e is equipped with only one turning motion regulating tangential threaded pin 41. This embodiment may also be equipped with the spring 14 or additionally with a turning motion fixing pin 20.

Figure 23:
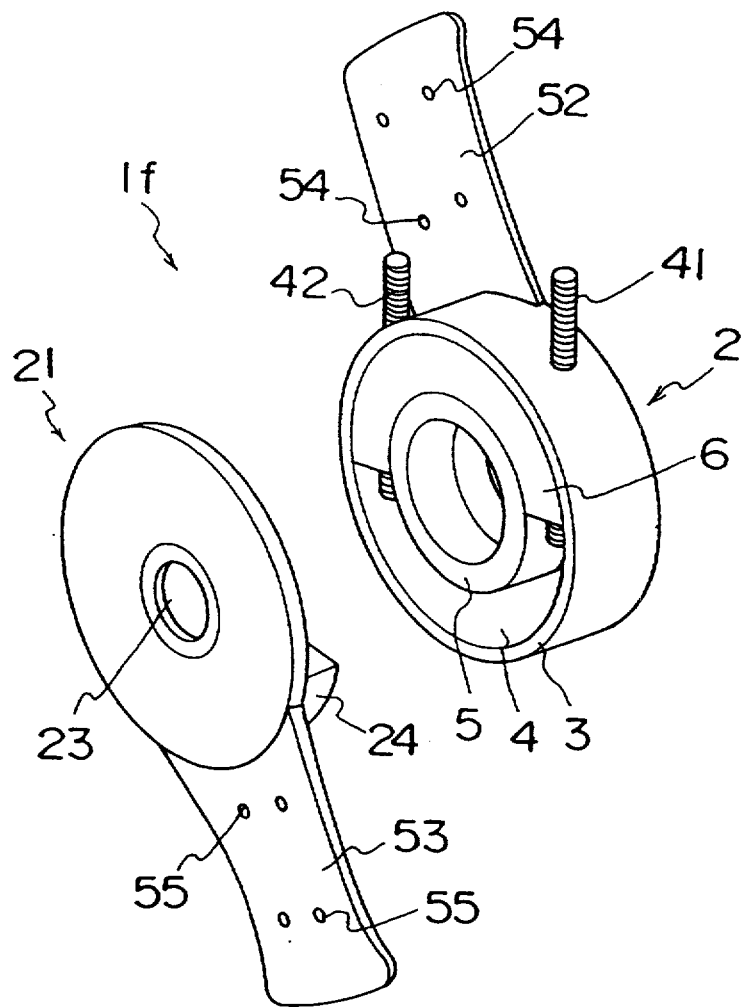
FIG. 23 is a perspective view showing an embodiment of the artificial limb joint device according to the present invention, in which the drive disc and the driven disc are individually formed integrally with body protecting member mounting portions.
Figure 24:
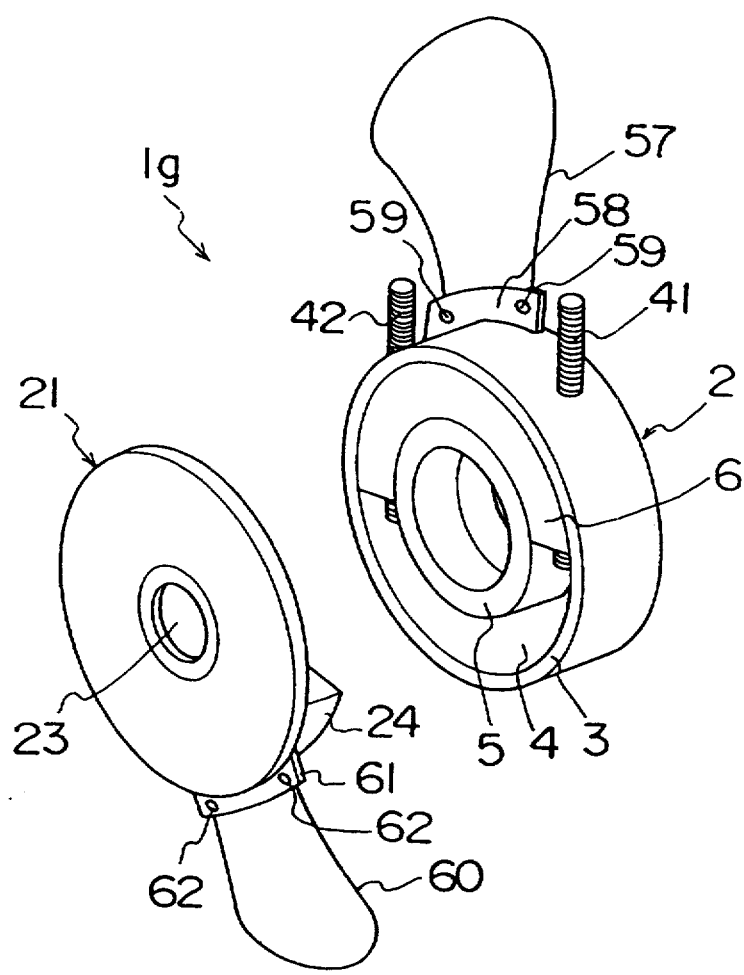
FIG. 24 is a perspective view showing a further embodiment of the artificial limb joint device according to the present invention, in which the drive disc and the driven disc are individually equipped with piano wire anchoring portions formed integrally with the body protecting member.

FIGS. 23 and 24 show further embodiments of the joint according to the present invention.

In a joint 1f shown in FIG. 23, the drive disc 2 and driven disc 21 are individually equipped with body protecting member mounting connectors 52 and 53. These connectors 52 and 53 may be either formed integrally with the drive disc 2 and the driven disc 21 or attached thereto by means of suitable connecting structures. The connectors 52 and 53 are formed with body protecting member mounting holes 54 and 55. This raises an advantage that the protecting members made of a synthetic resin or the like can have their rigidity and strength enhanced in the vicinity of the joint.

In a joint 1g shown in FIG. 24, the drive disc 2 and the driven disc 21 are individually equipped with piano wire anchoring tables 58 and 61. This embodiment of the joint 1g is useful in case reinforcing piano wires 57 and 60 are buried in or anchored at the corresponding body protecting members. Then, the end portions of the piano wires 57 and 60 may be fixed on the drive disc 2 and the driven disc 21 by means of screws 59 and 62 or the like. As in this embodiment, the artificial limb joint device is constructed such that the drive disc 2 and the driven disc 21 of the joint 1g are equipped with the piano wire anchoring tables 58 and 61 for connecting the body protecting members and such that the protecting members having the piano wires 57 and 60 buried or anchored therein are connected to the tables 58 and 61. Then, it is possible to enhance the strength, rigidity and flexibility of the protecting members and to increase the connecting strength between the protecting members and the drive disc 2 and the driven disc 21 of the joint 1g.

Figure 25:
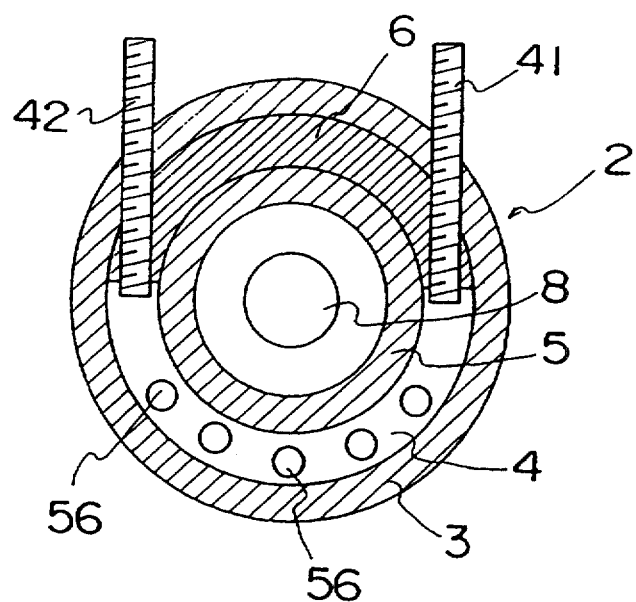
FIG. 25 is a longitudinally sectional side elevation showing the drive disc of an artificial limb joint device according to the present invention, as taken from the driven disc, in which the drive disc is formed in its end face formed with a plurality of holes for inserting fixing pins.
Figure 26:
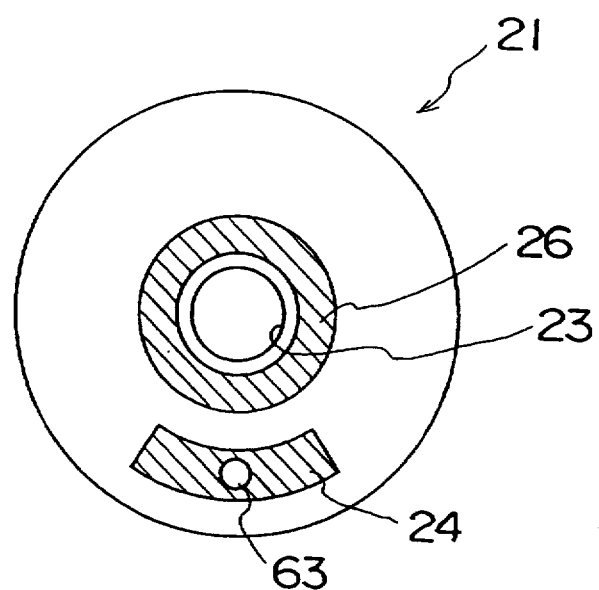
FIG. 26 is a longitudinally sectional side elevation taken from the drive disc of FIG. 25 and showing the driven disc which has its raised segment formed in its end face with a hole for the fixing pin.
Figure 27:
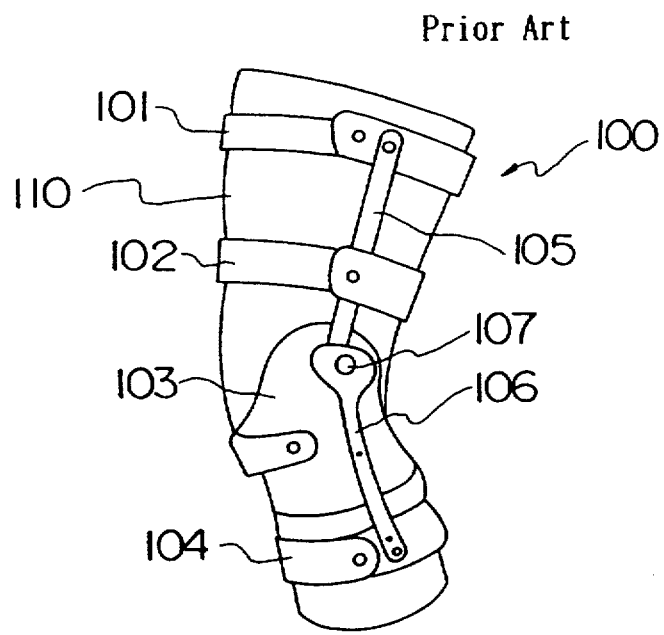
FIG. 27 is a perspective view showing one example of the artificial limb joint device well known in the prior art.
Figure 28:
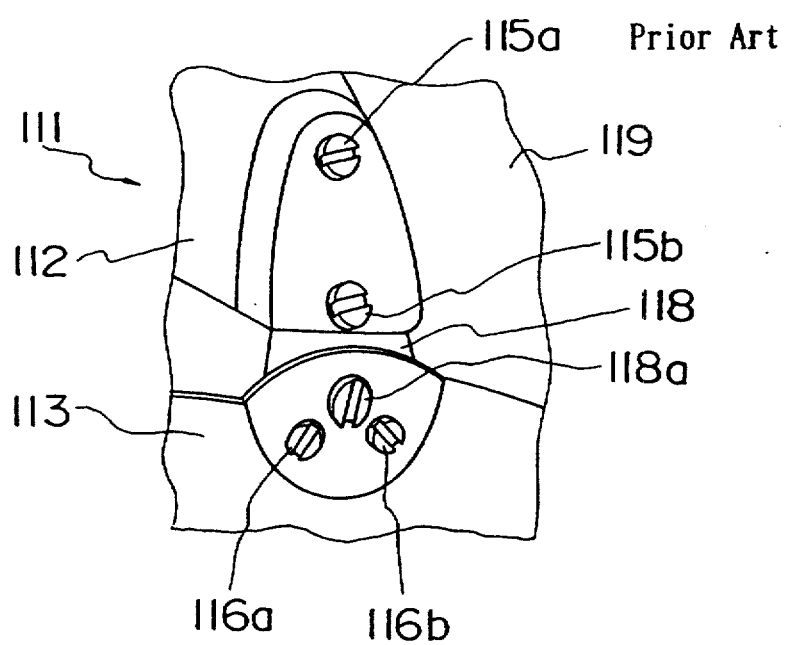
FIG. 28 is a perspective view showing an essential portion of the well-known artificial limb joint device having a joint of the USMC type.

Incidentally, in case the attachment to the body protecting members is carried out by using the connectors 52 and 53, as in the embodiment shown in FIG. 23, it is unnecessary to form the protecting member mounting threaded holes 12 in the end face of the drive disc 2, as shown in FIG. 2(B). In this case, therefore, the drive disc 2 may be formed with holes 56 for inserting a turning motion regulating pin, as shown in FIG. 25. Moreover, the driven disc 21 to be combined with such drive disc 2 may be formed in its raised segment 24 with a hole 63 for inserting a turning motion fixing pin, as shown in FIG. 26.

In the individual embodiments thus far described, the turning motion regulating threaded pins are arranged in parallel in case they are two in number. Despite of this fact, however, these two turning motion regulating threaded pins may be inclined to have their lading ends approaching or leaving each other. Then, the moving range of the raised segment is narrowed in the former case but is widened in the latter case. In either case, the moving range can be adjusted by those turning motion regulating threaded pins. Moreover, the moving range and adjusting range of the raised segment 24 can be arbitrarily determined in angular ranges by properly setting the diameter of the annular groove formed in the drive disc 2 of the joint, the angles and positions of the turning motion regulating threaded pins, the width of the annular groove 4, the size of the turning motion regulating threaded pins, and the length of the raised segment of the driven disc 21.

As has been described hereinbefore, the artificial limb joint device according to the present invention is constructed, with remarkably small size and light weight, of the drive disc and the driven disc. The allowable range of the relative turning motions between the adjoining body protecting members in the artificial limb joint device can be continuously and finely adjusted. Moreover, the joint device can be easily attached to the protecting members without deteriorating the flexibility of the protecting members made of a synthetic resin or the like.

The joint thus far described and the artificial limb joint device of the present invention using the joint have many advantages in use and manufacture, as follows:

1. The columned metal joint of the prior art has only a function to fix at a constant angle, and especially the joint device made of a synthetic resin is given the fixing function having no joint. On the contrary, the artificial limb joint device of the present invention has a moving angle adjusting function, which can be effected continuously and finely in the following manners: (a) the adjustment according to the recovery of troubles; (b) the adjustment according to the degree of deformation; and (c) the adjustment by a therapist in the clinical site for correcting and adjusting the moving angle, if necessary, any time and place and anyone without requiring the maker to repair or correct it. Moreover, the moving angle can be finely adjusted according to the degree of insertion of the turning motion regulating tangential pin into the drive disc of the joint.

2. The moving angle range and its adjusting range can be arbitrarily set by selecting the diameter of the drive disc and driven disc of the joint, the width of the annular groove, the thickness and position of the turning motion regulating pin, and the length of the raised segment of the driven disc. Moreover, the adjoining protecting members can be fixed at an arbitrary angle to improve the joint deformation and bad position of a patient.

3. In the artificial limb joint device using the existing spring joint, the spring force can be adjusted, but the moving range of the joint cannot be adjusted such that the moving range of the joint is the narrower for the stronger spring force but the wider for the weaker. According to the present joint, an arbitrary spring force can be achieved by selecting the diameter and thickness of the joint body, and the length, number of turns and diameter of the spring, and the moving range of the joint can be arbitrarily adjusted independently of the spring force. By applying the artificial limb joint device using this joint, therefore, the limb joints having aftereffects are promoted in their physical activities to improve the walking ability and the daily activities.

4. In case presumptions of the recovery from the troubles are insufficient, the devices prepared at an initial stage of clinic are frequently useless in the prior art and have to be made again according to the actual symptoms. The present joint is given many junctions to adjust the moving angle, to fix the angle and to act a power source so that it is promoted in the prevention of the joint deformation and the improvement in the bad position. As a result, only one device can prescribe the remedy from the initial to final stages consistently to perform a more effective treatment.

5. The synthetic resin joint of the prior art is weak in longitudinal, traverse and twisting directions and is not fixed in its machining because of a variety of manufacturing methods of makers, thus leaving problems in the durability of the joint body and the durability of the device body by the force applied thereto.

If the joint of the present invention is made of a metal, its body has an excellent durability and is connected and fixed to the protecting members of a synthetic resin at the two outer end faces of its drive disc and driven disc and by its center pin. As a result, the durability in the longitudinal, traverse and twisting directions can be drastically improved to eliminate the problem of breakage.

6. The joint of the prior art cannot be manufactured by other than a specific maker, but the present joint can be ready-made by preparing a variety of types for applications so that it can eliminate difficulties in the techniques and skills for the manufacturing the joint devices.

7. Since the present joint is used without being attached or connected to any metal column, its weight can be reduced. Moreover, the joint itself can be connected to the portions of the protecting members without any loss of its characteristics even if the protecting members are made of a synthetic resin or the like. Thus, the joint will not deteriorate the physical twisting motions of the human body.

8. Since the present joint is integrated with another material including the metal column, the deformation correcting force is augmented by its fine angle adjustment and doubled strength. Thus, the severe deformation which could not be corrected in the prior art can be remedied to extend drastic remedy techniques.

9. Thanks to the light weight and the multiple functions including the connections, the present joint can be assembled into the artificial limb joint device of a synthetic resin without deteriorating the appearance.

10. Thus, the joint according to the present invention and the artificial limb joint device using the joint can achieve the functions to improve the physical activities in the above-specified various fields with the resultant effects and can lead to metal effects of the troubled patients.

What is claimed is:

1. An artificial limb joint device for hinging adjoining body protecting members to turn on an axis perpendicular to the longitudinal axes of the body, protecting members, comprising: a drive disc; a driven disc; a joint pin extending through the individual centers of said drive disc and said driven disc, said drive disc being detachably engageable with one of the adjoining body protecting members and including an outer flange, and an inner flange disposed radially inside of said outer flange and defining an annular groove in the end face of said drive disc together with said outer flange, said outer flange being formed with a through hole extending in a tangential direction of said annular groove, said driven disc being detacheably engageable with the other of the body protecting members and formed with such a raised segment at the end face confronting said drive disc as to engage in a sliding manner with the annular groove of said drive disc; and a turning motion regulating pin inserted into said through hole to come into and out of said annular groove, for regulating the turning motions of said raised segment in said annular groove.

2. An artificial limb joint device according to claim 1, wherein the through hole formed in the outer flange of said drive disc is internally threaded, and wherein said turning motion regulating pin is so externally threaded as to be driven into said threaded through hole.

3. An artificial limb joint device according to claim 1 or 2, wherein said through hole is formed in only one portion of the outer flange of said drive disc, and wherein said turning motion regulating pin is inserted into said through hole.

4. An artificial limb joint device according to claim 1 or 2, wherein said through hole is formed in two portions of the outer flange of said drive disc, and wherein said turning motion regulating pin is inserted into each of said two through holes.

5. An artificial limb joint device according to claim 1, further comprising a turning motion regulating block member fitted in the annular groove of said drive disc for regulating the turning motions of the raised segment of said driven disc in said annular groove.

6. An artificial limb joint device according to claim 5, wherein said turning motion regulating pin disposed in said drive disc is inserted from the through hole of said outer flange through said turning motion regulating block member to come into and out of said annular groove.

7. An artificial limb joint device according to claim 1 or 5, further comprising a compression spring mounted in such a space between the turning motion regulating pin or the turning motion regulating block member of said drive disc and the raised segment of said driven disc as is formed in the annular groove of said drive disc when said drive disc and said driven disc are assembled.

8. An artificial limb joint device according to claim 1 or 5, further comprising a tension spring mounted in such a space between the turning motion regulating pin or the turning motion regulating block member of said drive disc and the raised segment of said driven disc as is formed in the annular groove of said drive disc when said drive disc and said driven disc are assembled, and wherein said tension spring has its one end connected to said turning motion regulating pin or said turning motion regulating block member and its other end connected to said raised segment.

9. An artificial limb joint device according to claim 1 or 5, further comprising a turning motion regulating pin, in addition to said turning motion regulating pin and said turning motion regulating block member, for being inserted radially of said drive disc from a through hole, which is formed in the portion of said outer flange in the annular groove of said drive disc, and into a hole which is formed in the corresponding portion of said inner flange.

10. An artificial limb joint device according to claim 9, wherein said hole for receiving said turning motion regulating pin in the radial direction is formed in a plurality of portions of the outer and inner flanges of the annular groove of said drive disc.

11. An artificial limb joint device according to claim 9, wherein the turning motion regulating pins to be inserted radially of said drive disc are turning motion fixing pins for fixing the turning motions of the raised segment of said driven disc between the tangential turning motion regulating pin and said turning motion regulating block member.

12. An artificial limb joint device according to claim 9, wherein the raised segment of said driven disc is formed with a radial through hole so that said turning motion fixing pin can be inserted from the through hole, which is formed in the outer flange portion of the annular groove of said drive disc, and through the through hole, which is formed in said raised segment, into the hole which is formed in the inner flange portion of said annular groove.

13. An artificial limb joint device according to claim 1, wherein said drive disc and said driven disc are formed in their individual outer end faces with threaded holes for mounting said body protecting members.

14. An artificial limb joint device according to claim 1, wherein said drive disc and said driven disc are individually formed with connectors extending therefrom for mounting said body protecting members.

15. An artificial limb joint device according to claim 1, wherein said driven disc is formed on the inner side of said raised segment with an annular land engaging with the inner face of the inner flange of the annular land of said drive disc.

16. An artificial limb joint device according to claim 1, wherein one of said adjoining body protecting members is attached to said drive disc whereas the other of said body protecting members is attached to said driven disc, and wherein said body protecting members are made flexible of a synthetic resin.

17. An artificial limb joint device according to claim 16, further comprising reinforcing piano wires buried or anchored in said body protecting members and fixed to said drive disc and said driven disc.

* * * * *